(12) United States Patent
Dahanukar et al.

(10) Patent No.: US 7,192,962 B2
(45) Date of Patent: Mar. 20, 2007

(54) XANTHINE PHOSPHODIESTERASE V INHIBITOR POLYMORPHS

(75) Inventors: Vilas H. Dahanukar, Edison, NJ (US); Hoa N. Nguyen, Dayton, NJ (US); Cecilia A. Orr, Clark, NJ (US); Funcheng Zhang, Edison, NJ (US); Ilia A. Zavialov, East Windwor, NJ (US); Kevin Klopfer, Flemington, NJ (US); Jeffrey M. Skell, Holliston, MA (US); Albert W. Buchholz, Jr., Bridgewater, NJ (US); Craig D. Boyle, Branchburg, NJ (US)

(73) Assignee: Schering Corporation, Kenilworth, NJ (US)

( * ) Notice: Subject to any disclaimer, the term of this patent is extended or adjusted under 35 U.S.C. 154(b) by 7 days.

(21) Appl. No.: 10/449,650

(22) Filed: May 30, 2003

(65) Prior Publication Data

US 2003/0232845 A1 Dec. 18, 2003

Related U.S. Application Data

(60) Provisional application No. 60/384,484, filed on May 31, 2002.

(51) Int. Cl.
- A07D 473/04 (2006.01)
- A61K 31/522 (2006.01)
- A61P 9/12 (2006.01)
- A61P 15/10 (2006.01)

(52) U.S. Cl. .................... 514/263.31; 514/263.32; 514/263.36; 544/272

(58) Field of Classification Search .................... None
See application file for complete search history.

(56) References Cited

U.S. PATENT DOCUMENTS 6,469,012 B1 10/2002 Ellis et al. ................ 514/258
2006/0205943 A1* 9/2006 Dahanukar et al. ......... 544/267

FOREIGN PATENT DOCUMENTS

WO  WO 099/20625    4/1999
WO  WO 02/24698 A1  3/2002

OTHER PUBLICATIONS

International Search Report, May 30, 2003, PCT/US03/16890.

* cited by examiner

Primary Examiner—Mark L. Berch
(74) Attorney, Agent, or Firm—H. Eric Fischer; Gerard E. Reinhardt

(57) ABSTRACT

Crystalline polymorphs of 1-ethyl-3,7-dihydro-8-[(1R,2R)-(hydroxycyclopentyl)amino]-3-(2-hydroxyethyl)-7-[(3-bromo-4-methoxyphenyl)methyl]-1H-Purine-2,6-dione in Form 1 and Form 2, which exhibit x-ray powder diffraction profiles substantially the same as those shown in FIGS. 5 and 6, respectively, and which exhibit differential scanning calorimtery profiles substantially the same as those shown in FIGS. 2 and 4, respectively, and are represented by the formula:

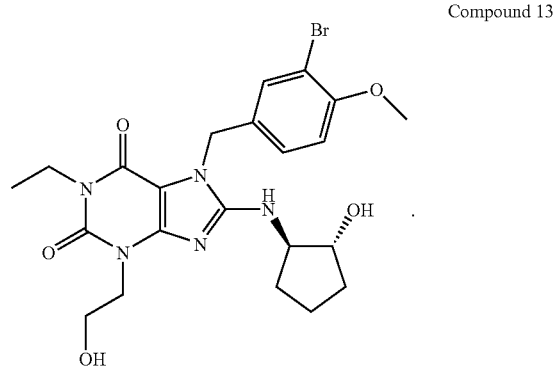

Compound 13

Pharmaceutical compositions comprising the polymorph Form 1 or 2 of Compound 13 and at least one excipient or carrier, and methods of using the polymorph Form 1 or 2 of Compound 13 to treat a variety of physiological disorders, such as erectile dysfunction.

26 Claims, 6 Drawing Sheets

XANTHINE PHOSPHODIESTERASE V INHIBITOR POLYMORPHS

CROSS-REFERENCE TO RELATED PATENT APPLICATION

The present application claims priority under 35 USC section 119(e) to U.S. Provisional application Ser. No. 60/384,484, filed May 31, 2002, which is incorporated by reference herein as if fully set forth.

BACKGROUND OF THE INVENTION

1. Field of Invention

The invention relates to crystalline polymorphs of a polycyclic xanthine phosphodiesterase ("PDE") V inhibitor.

2. Background

WO 02/24698, which is incorporated herein by reference in its entirety, teaches a class of xanthine PDE V inhibitor compounds useful for the treatment of impotence. A general process disclosed therein (page 75, line 6 to page 80, line 2) for preparing xanthine PDE V inhibitor compounds having the formula (I) follows:

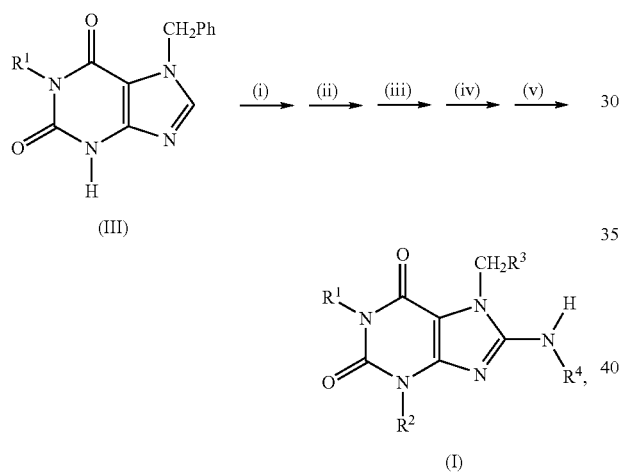

(i) reacting a compound having the formula (III) with an alkyl halide in the presence of a base (introduction of $R^2$ or a protected form of $R^2$);

(ii) (a) debenzylating and then (b) alkylating the compound resulting from step (i) with an alkyl halide, $XCH_2R^3$;

(iii) (a) deprotonating and then (b) halogenating the compound resulting from step (ii);

(iv) reacting the compound resulting from step (iii) with an amine having the formula $R^4NH_2$; and (v) removing a protecting portion of $R^2$, if present, on the compound resulting from step (iv) to form the compound having the formula (I).

$R^1$, $R^2$, $R^3$ and $R^4$ are each defined in WO 02/24698.

WO 02/24698 (pages 44 & 68–73) further teaches a synthesis for a specific xanthine PDE V inhibitor compound identified therein as Compound 13 or Compound 114 of Table II. Compound 13 can be named as 1-ethyl-3,7-dihydro-8-[(1R,2R)-(hydroxycyclopentyl)amino]-3-(2-hydroxyethyl)-7-[(3-bromo-4-methoxyphenyl)methyl]-1H-Purine-2,6-dione:

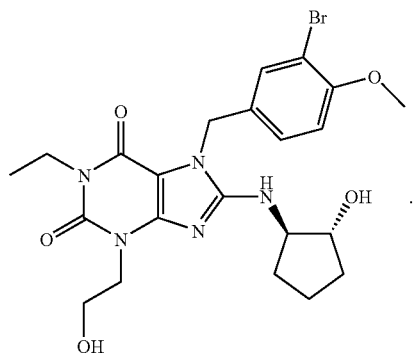

Compound 13

Compound 13 exhibits good PDE V inhibitor activity (potency) and selectivity, and is useful for treating erectile dysfunction. However, when made according to the process described in WO 02/24698, Compound 13 can exhibit some undesirable properties with respect to thermodynamic stability.

Polymorphism can be characterized as the ability of a compound to crystallize into different crystal forms, while maintaining the same chemical formula. Polymorphs of a given drug substance are chemically identical in containing the same atoms bonded to one another in the same way, but differ in their crystal forms, which can affect one or more physical properties, such as solubility, melting point, bulk density, flow properties, etc.

It would be beneficial to improve the thermodynamic properties of Compound 13. It would further be beneficial to produce Compound 13 in a stable crystalline form, which has consistent physical properties. The invention seeks to provide these and other benefits, which will become apparent as the description progresses.

SUMMARY OF THE INVENTION

The invention provides two crystalline polymorphs of Compound 13. A crystalline polymorph can be identified by its x-ray powder diffraction pattern expressed in terms of "2θ Angles (°)."

One aspect of the invention provides a crystalline polymorph Form 2 of Compound 13:

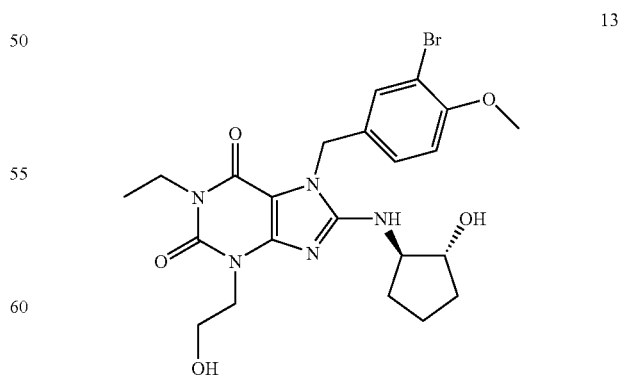

13 that exhibits an x-ray powder diffraction pattern having characteristic peak locations of 8.1, 11.3, 17.2, and 22.2 degrees 2θ+/−0.5 degrees 2θ.

Another aspect of the invention provides crystalline polymorph Form 2 of Compound 13, which exhibits an x-ray powder diffraction pattern having characteristic peak locations of 8.1, 11.3, 13.1, 15.3, 16.1, 17.2, 17.6, 18.9, 20.9, 21.8, 22.2, 23.4 24.1, 25.8 and 30.6 degrees 2θ+/−0.5 degrees 2θ.

Another aspect of the invention provides crystalline polymorph Form 2 of Compound 13, which exhibits an x-ray powder diffraction pattern substantially the same as the x-ray powder diffraction pattern shown in FIG. 5.

Another aspect of the invention provides crystalline polymorph Form 2 of Compound 13, which exhibits a differential scanning calorimetry pattern substantially the same as the differential scanning calorimetry pattern shown in FIG. 2.

The invention comprises polymorph Form 2 of Compound 13 and any isomer e.g., enantiomer, stereoisomer, rotomer and tautomer, thereof.

Another aspect of the invention provides crystalline polymorph Form 1 of Compound 13 that exhibits an x-ray powder diffraction pattern having characteristic peak locations of 7.3, 9.2 and 20.2 degrees 2θ+/−0.5 degrees 2θ.

Another aspect of the invention provides crystalline polymorph Form 1 of Compound 13, which exhibits an x-ray powder diffraction pattern having characteristic peak locations of 7.3, 8.4, 9.2, 12.7, 14.3, 15.0, 15.4, 16.5, 18.8, 20.2, 20.9, 24.0, 25.8, 26.4, 27.2, 27.6, 29.3, 31.9 and 34.6 degrees 2θ+/−0.5 degrees 2θ.

Another aspect of the invention provides crystalline polymorph Form 1 of Compound 13, which exhibits an x-ray powder diffraction pattern substantially the same as the x-ray powder diffraction pattern shown in FIG. 6.

Another aspect of the invention provides crystalline polymorph Form 1 of Compound 13, which exhibits a differential scanning calorimetry pattern substantially the same as the differential scanning calorimetry pattern shown in FIG. 4.

The invention comprises polymorph Form 1 of Compound 13 and any isomer, e.g., enantiomer, stereoisomer, rotomer and tautomer, thereof.

Other aspects of the invention comprise pharmaceutically-acceptable compositions prepared from the inventive polymorphs. The inventive compounds can be useful for treating a variety of diseases, symptoms and physiological disorders, such as sexual dysfunction (e.g., impotence).

A further understanding of the invention will be had from the following drawings, description and claims.

DETAILED DESCRIPTION

As used above, and throughout the specification, the following terms, unless otherwise indicated, shall be understood to have the following meanings:

"Patient" includes both human and other animals.

"Mammal" includes humans and other mammalian animals.

"Alkyl" means an aliphatic hydrocarbon group which may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched means that one or more lower alkyl groups such as methyl, ethyl or propyl, are attached to a linear alkyl chain. The alkyl group can be substituted by one or more substituents which may be the same or different. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Aryl" means an aromatic monocyclic or multicyclic ring system comprising about 6 to about 14 carbon atoms, preferably about 6 to about 10 carbon atoms. The aryl group can be optionally substituted with one or more ring system substituents which may be the same or different. Non-limiting examples of suitable aryl groups include phenyl and naphthyl.

"Polymorph" means a crystalline form of a substance that is distinct from another crystalline form but that shares the same chemical formula.

"Relative Intensity" means the intensity of a peak relative to the intensity of the largest peak measured in an x-ray powder diffraction analysis. The relative intensity can be calculated as either the ratio of the heights of the peaks (measured in counts per second) or the ratio of the areas of the peaks. Relative intensity data presented herein are calculated as the ratios of the heights of the peaks.

"Anti-solvent" means a substance that reduces the solubility of a solute in a solvent.

"c-GMP" means cyclic guanosine monophosphate.

"Alcohol" means an organic compound containing a hydroxyl group (—OH).

"Nitrile" means an organic compound containing a —C≡N group.

"Ester" means an organic compound containing an RC(O)OR group, wherein the R's are independently alkyl or aryl and the parentheses indicate that the enclosed O is double-bonded to the C.

"Ketone" means an organic compound containing a carbonyl group (C=O) attached to two alkyl groups.

"Excipient" means an essentially inert substance used as a diluent or to give form or consistency to a formulation.

"Hydrocarbon" means an organic compound consisting of carbon and hydrogen.

Polymorphs of Compound 13

Figure 1:
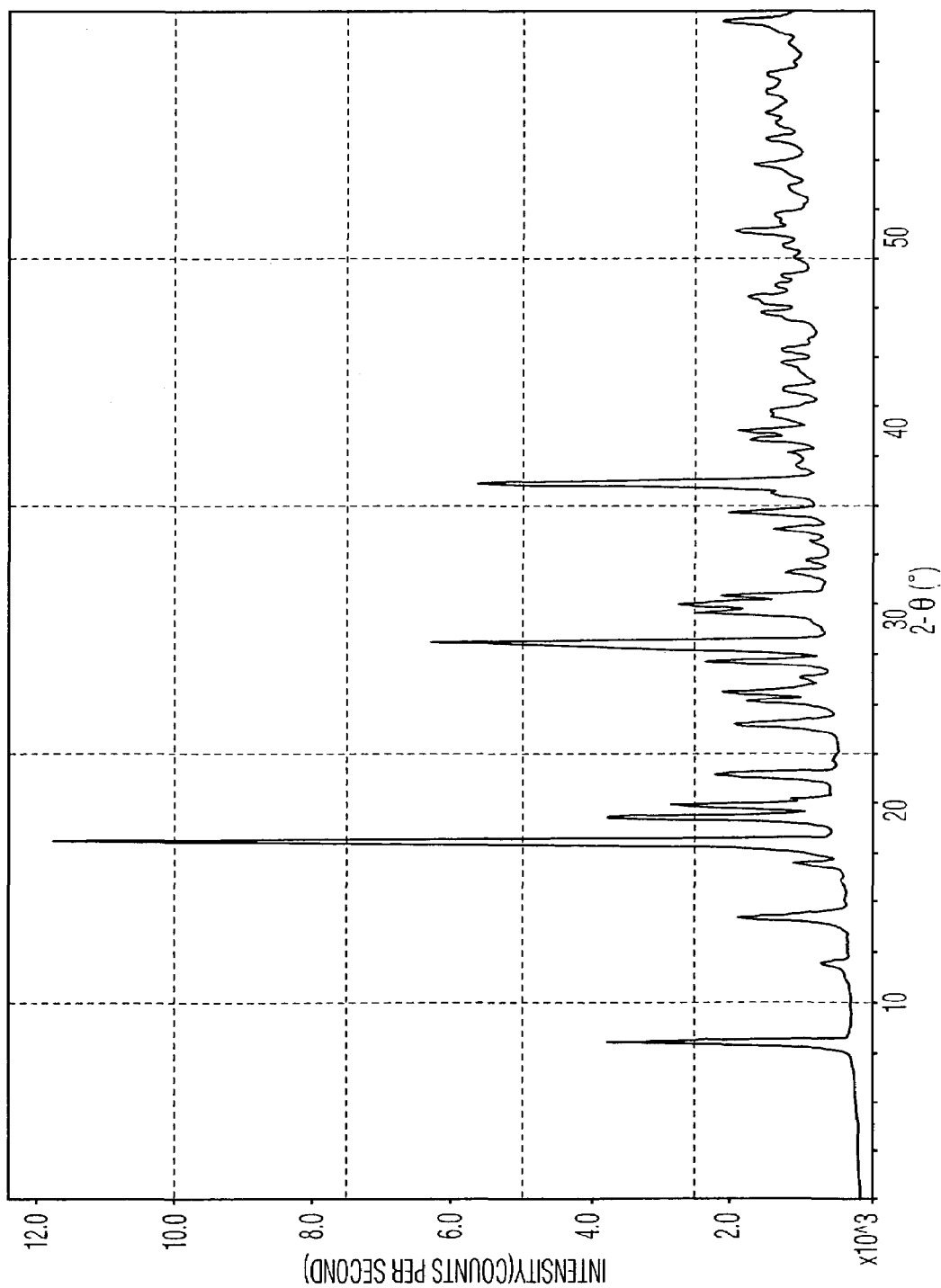
FIG. 1 is a graph of an x-ray powder diffraction pattern of crystalline polymorph Form 2 of Compound 13 crystallized from acetonitrile. The graph plots the intensity of the peaks as defined by counts per second versus the diffraction angle 2θ in degrees. The sample was unmicronized and not packed in the sample holder. The data were generated on a Rigaku MiniFlex diffractometer.
Figure 2:
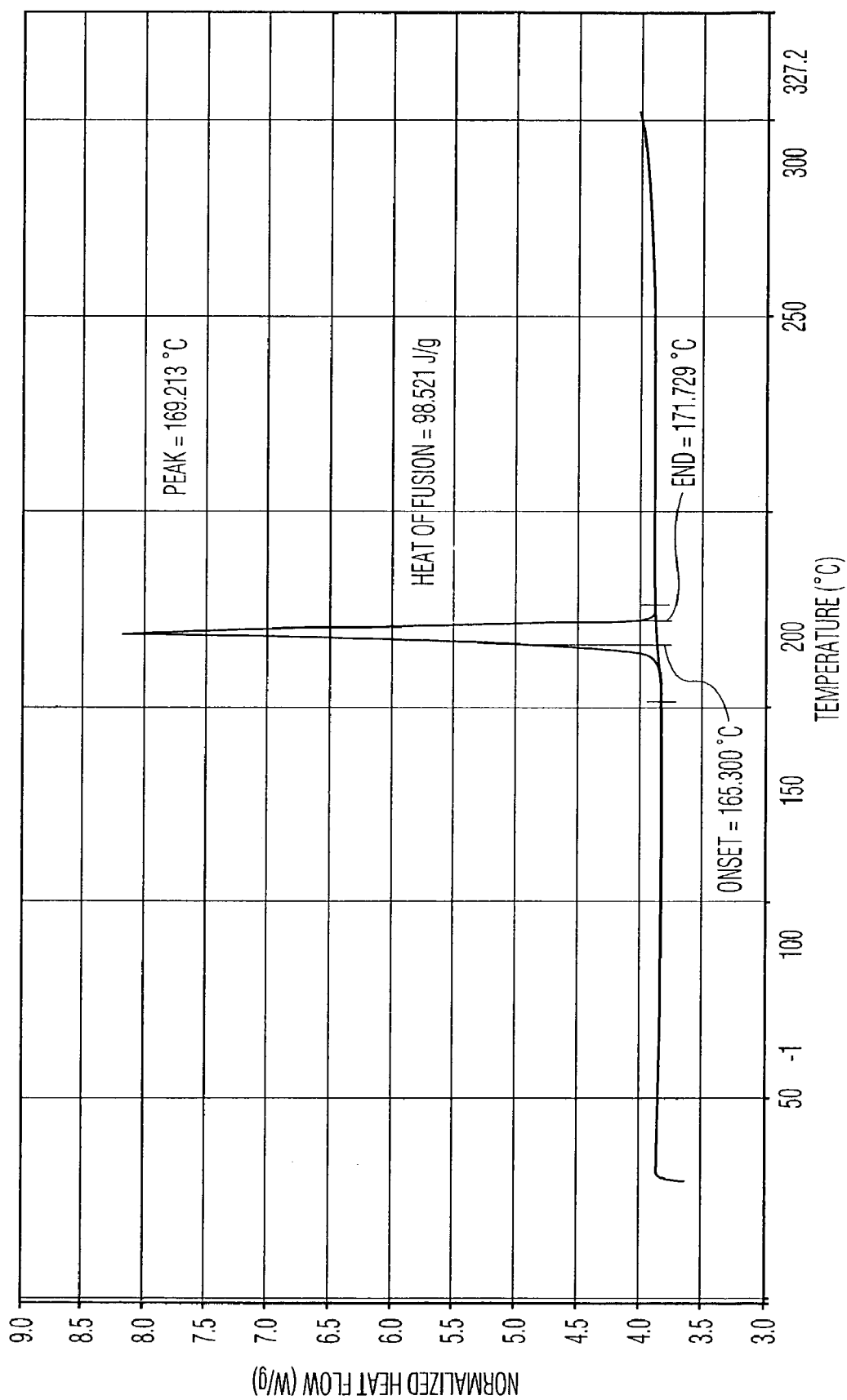
FIG. 2 is a graph of a differential scanning calorimetry pattern of crystalline polymorph Form 2 of Compound 13 crystallized from acetonitrile. The graph plots the normalized heat flow in units of Watts/gram ("W/g") versus the measured sample temperature in degrees C.
Figure 3:
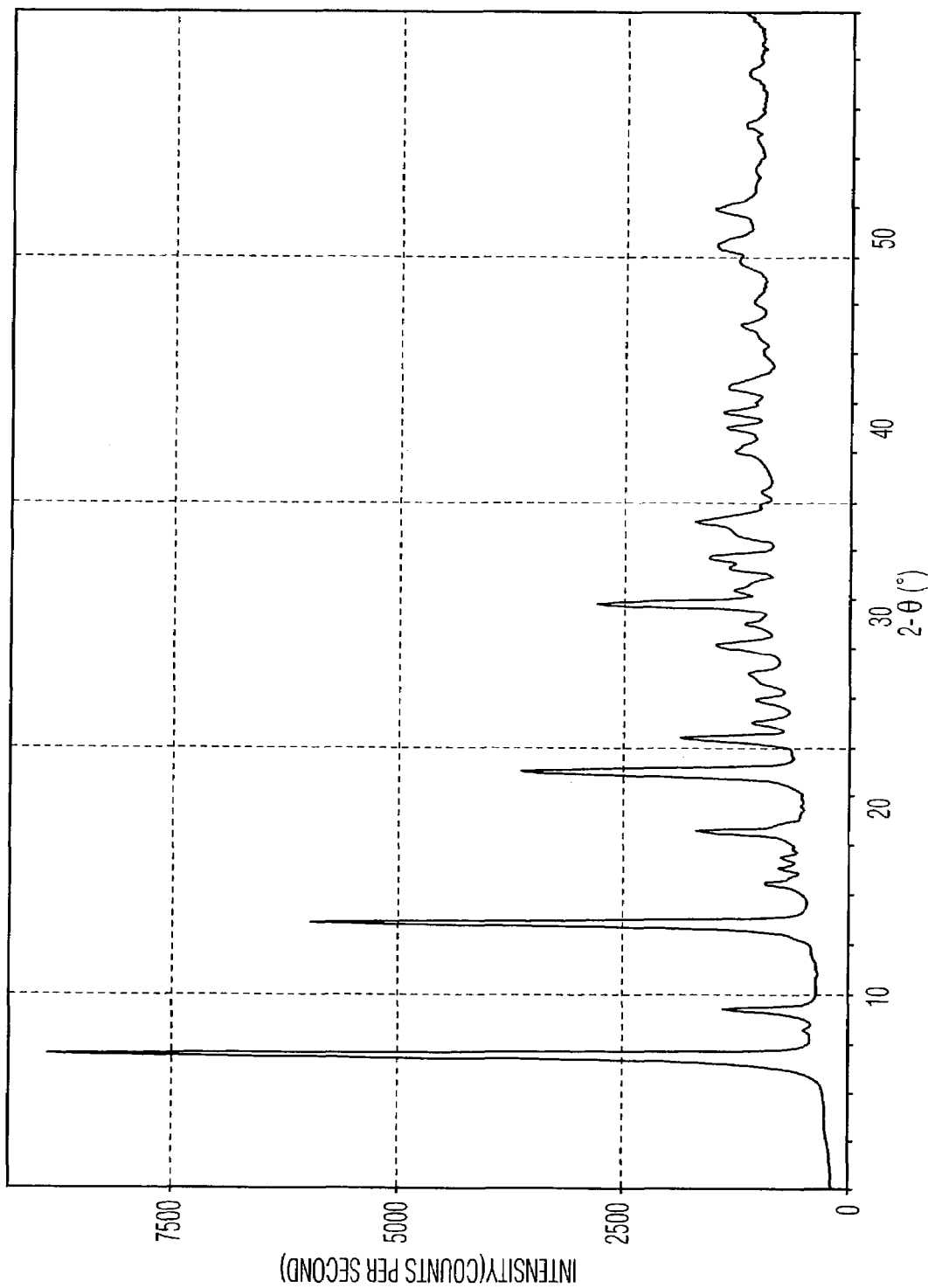
FIG. 3 is a graph of an x-ray powder diffraction pattern of crystalline polymorph Form 1 of Compound 13 crystallized from methanol/water. The graph plots the intensity of the peaks as defined by counts per second versus the diffraction angle 2θ in degrees. The sample was unmicronized and not packed in the sample holder. The data were generated on a Rigaku MiniFlex diffractometer.
Figure 4:
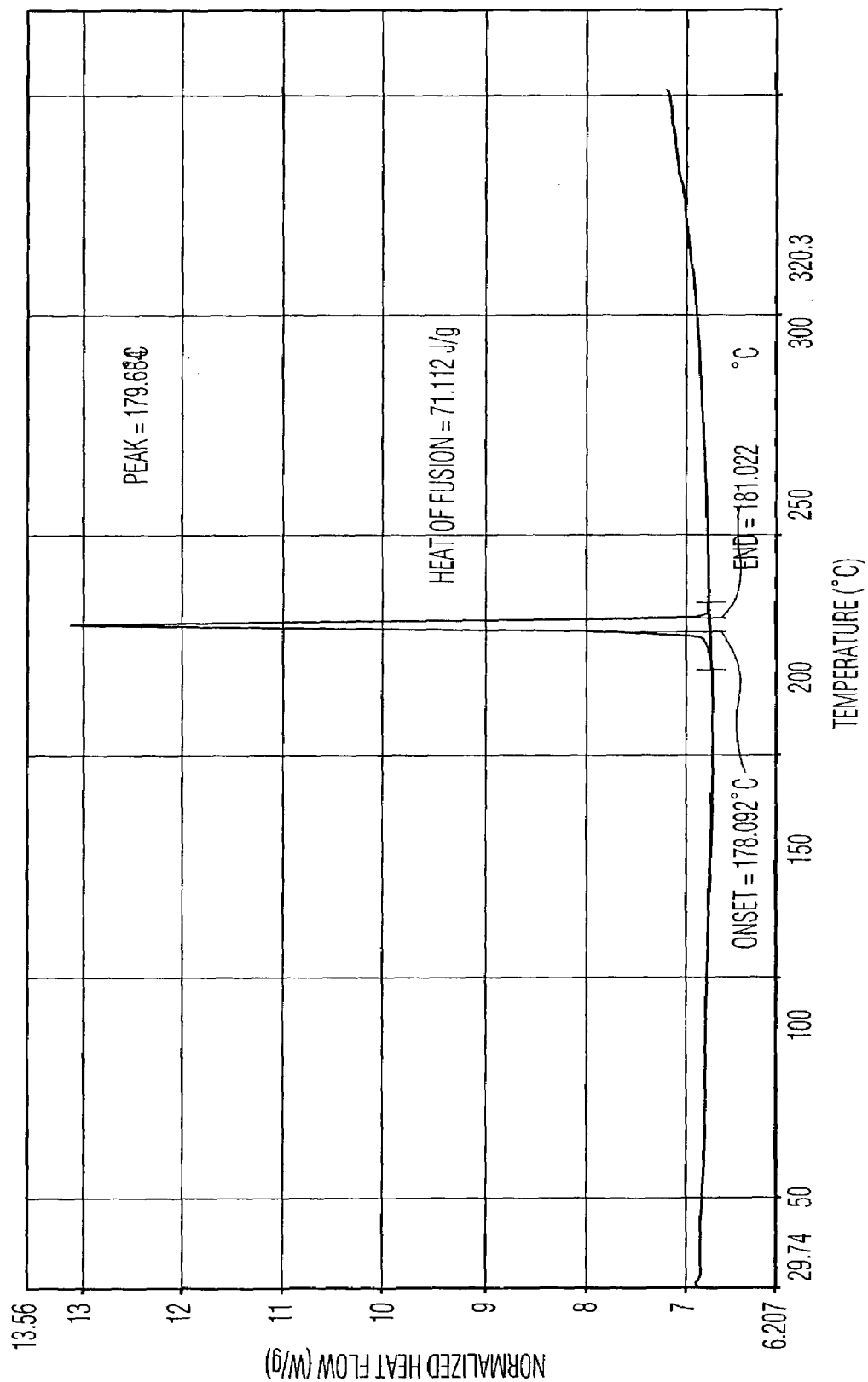
FIG. 4 is a graph of a differential scanning calorimetry pattern of crystalline polymorph Form 1 of Compound 13 crystallized from methanol/water. The graph plots the normalized heat flow in units of Watts/gram ("W/g") versus the measured sample temperature in degrees C.

Compound 13 can exist in at least two distinct crystalline polymorphic forms, each having distinct physical properties. These two different crystalline polymorphs of Compound 13 have been identified as Form 1 and Form 2. Forms 1 and 2 of Compound 13 can be characterized by x-ray powder diffraction (FIGS. 1, 3, 5 and 6) and/or differential scanning calorimetry (FIGS. 2 and 4).

Analytical Methodology for Chemical Identification of Polymorphs

Samples of the two polymorphs—Forms 1 and 2 of Compound 13—were analyzed as dry powders for x-ray powder diffraction ("XRPD") and differential scanning calorimetry ("DSC") analyses. The samples were analyzed with minimal preparation to prevent any form changes. The samples were lightly rubbed to insure that particles were not clumped together. No solvents, drying or other preparation steps were used for these analyses. The XRPD and DSC data can each uniquely identify Forms 1 and 2 of Compound 13.

A number of XRPD analyses were performed using a variety of analyzers. Some of the samples were micronized, while others were not. One set of measurements was made using a Rigaku MiniFlexe diffractometer (manufactured in 1999) that rotated the specimen at 54 revolutions per minute ("rpm") to reduce preferred orientations of the crystals. The polymorph samples were supplied in powder form and were placed onto a face of a Si-coated low background scatter aluminum plate using a hand held dowel with a minimum of force. A crystalline silicon standard was used to check peak position accuracy. The samples were exposed to ambient conditions. The x-ray patterns presented in FIGS. 1 and 3 are filtered with a nine-point Savitzky-Golay parabolic filter, but otherwise are essentially raw patterns without a background correction or a K-α2 peak removal. The counts presented on the y-axes of FIGS. 1 and 3 plots are in units of counts per second. The instrument uses a variable divergence slit with a θ/2θ scan axis configuration. The intensity of the peaks (y-axis is in counts per second) is plotted versus the 2θ angle (α-axis is in degrees 2θ). The data of FIGS. 1 and 3 were plotted with detector counts normalized for the collection time per step versus the 2θ angle. The data were evaluated using JADE® pattern processing software version 5.0 from Materials Data Inc. ("MDI"). The software automatically does a final filtering, fits a background, and measures the area and height of each peak. The relative peak intensities are calculated using a ratio of the height of each reported peak to the height of the largest peak measured. The relative peak intensities used were directly equal to the filtered counts per second of the raw data. Form 2 of Compound 13 (FIG. 1) and Form 1 of Compound 13 (FIG. 3) each exhibited unique XRPD patterns. X-ray powder diffraction is discussed in the *Encyclopedia of Analytic Science*, Alan Townshend, ed., vol. 9, pp. 5585–5593, Academic Press, London (1995), which is incorporated herein by reference.

Using the Rigaku MiniFlex® diffractometer and the above-described methods, it was found that crystalline polymorph Form 2 of Compound 13 exhibits an x-ray powder diffraction pattern as shown in FIG. 1. The relative intensities and the 2θ angle locations of the characteristic peaks of FIG. 1 are displayed in TABLE 1:

TABLE 1

| | Form 2 of Compound 13 | |
|---|---|---|
| 2θ Angle (°) | Relative Intensity (% Height) | Relative Intensity (Peak Strength) |
| 8.44 | 31.1 | S |
| 11.54 | 3.6 | VW |
| 13.36 | 13.9 | M |
| 15.56 | 5.2 | W |
| 16.42 | 100.0 | S |
| 17.44 | 28.3 | S |
| 17.92 | 20.3 | S |
| 19.18 | 15.2 | M |
| 21.20 | 12.8 | M |
| 22.12 | 10.1 | M |
| 22.50 | 13.9 | M |
| 23.06 | 2.8 | VWD |
| 23.70 | 15.3 | M |
| 24.46 | 50.1 | S |
| 25.70 | 16.5 | M |
| 26.04 | 18.4 | M |
| 26.40 | 12.3 | M |
| 27.34 | 5.1 | W |
| 27.86 | 3.0 | VW |
| 28.58 | 2.2 | VW |
| 29.08 | 6.4 | W |
| 29.74 | 11.2 | M |
| 30.48 | 5.5 | W |
| 30.88 | 43.2 | S |
| 31.62 | 2.2 | VW |
| 32.14 | 3.1 | W |
| 32.68 | 7.6 | W |
| 33.02 | 8.7 | W |
| 33.82 | 5.2 | WD |
| 34.68 | 4.3 | W |
| 35.78 | 4.2 | W |
| 36.30 | 3.9 | VW |
| 37.78 | 4.6 | W |
| 38.44 | 7.0 | WD |
| 38.86 | 3.4 | VW |
| 39.28 | 2.1 | VW |
| 40.04 | 1.1 | VWD |
| 40.48 | 1.9 | VW |
| 41.08 | 8.5 | W |
| 41.72 | 3.7 | W |
| 42.88 | 2.0 | WD |
| 43.76 | 6.2 | W |
| 44.76 | 4.1 | W |
| 45.40 | 2.3 | VWD |
| 45.82 | 3.2 | VWD |
| 46.72 | 3.0 | VWD |
| 47.44 | 3.5 | VWD |
| 48.68 | 1.0 | VWD |
| 49.60 | 8.9 | W | wherein peak strengths categorize relative intensities according to the following scheme: S is Strong (20.0–100.0%); M is Medium (9.0–19.9%); W is Weak (4.0–8.9%); VW is Very Weak (0.1–3.9%); and VWD is Very Weak and Diffuse (broad).

Using the Rigaku MiniFlex® diffractometer and the above-described methods, it was found that crystalline polymorph Form 1 of Compound 13 exhibits an x-ray powder diffraction pattern as shown FIG. 3. The relative intensities and the 2θ angle locations of the characteristic peaks of FIG. 3 are displayed in TABLE 2:

TABLE 2

Form 1 of Compound 13

| 2θ Angle (°) | Relative Intensity (% Height) | Relative Intensity (Peak Strength) |
|---|---|---|
| 7.48 | 100.0 | S |
| 8.52 | 0.9 | VW |
| 9.36 | 11.7 | M |
| 12.84 | 64.8 | S |
| 14.44 | 4.8 | WD |
| 15.10 | 2.7 | VWD |
| 15.52 | 2.2 | VWD |
| 16.58 | 13.2 | M |
| 19.02 | 35.8 | S |
| 20.34 | 14.4 | M |
| 21.00 | 4.7 | W |
| 21.94 | 4.1 | W |
| 22.70 | 3.1 | VWD |
| 22.98 | 4.5 | WD |
| 24.14 | 7.8 | W |
| 25.04 | 3.1 | VWD |
| 25.84 | 21.8 | S |
| 26.40 | 4.5 | W |
| 27.32 | 5.8 | W |
| 27.74 | 8.4 | W |
| 28.78 | 4.5 | WD |
| 29.20 | 9.9 | M |
| 30.40 | 1.2 | VWD |
| 32.08 | 3.4 | W |
| 33.02 | 4.3 | W |
| 33.66 | 5.1 | W |
| 34.63 | 5.0 | WD |
| 37.24 | 3.3 | VWD |
| 38.12 | 1.7 | VWD |
| 40.46 | 4.8 | W |
| 41.94 | 5.1 | W |
| 45.44 | 2.3 | WD |
| 47.52 | 2.3 | WD | wherein peak strengths are categorized according the scheme described above.

The XRPD analyses were repeated using different analytic equipment. Rigaku DMAX 2200 and Bruker D8 diffractometers were used to collect the XRPD data. In these analyses, the samples were packed into the sample holders in such a way as to reduce measurement error that might result from uneven sample surfaces or inconsistent sample thicknesses.

The Rigaku DMAX-2200 diffractometer (manufactured in 1998) was operated with a take-off angle of 6 degrees and automatic, variable divergence slits. The beam width was 20 mm. The apparatus uses a graphite monochromator and a scintillation detector. During scanning, the step size was 0.02 degrees over a step duration of 0.3 seconds. Scanning speed was 4 degrees per minute. The sample spin rate was 40 rpm.

The Bruker D8 diffractometer (manufactured in 2002) has a parallel optic configuration with a GÖBEL beam focusing mirror and a PSD detector equipped with a fixed radial soller slit was used with an Anton Paar TTK450 temperature stage. The divergence slits are fixed at 0.6 mm. The sample holder was a top-loading brass block. Specimens were leveled using a glass microscope slide. The sample chamber was not purged, not heated above 30 deg. C., and not under vacuum. Instrument calibration was verified using mica standards. During scanning, the step size was 0.013 degrees over step durations of 0.1 and 0.5 seconds. Data smoothing was accomplished using EVA analysis software, version 7.0, supplied by Bruker® written by SOCABIM®. The data were filtered with a Fast Fourier smoothing program (20.000×1). The radiation sources for all three diffractometers are copper (Kα).

Figure 5:
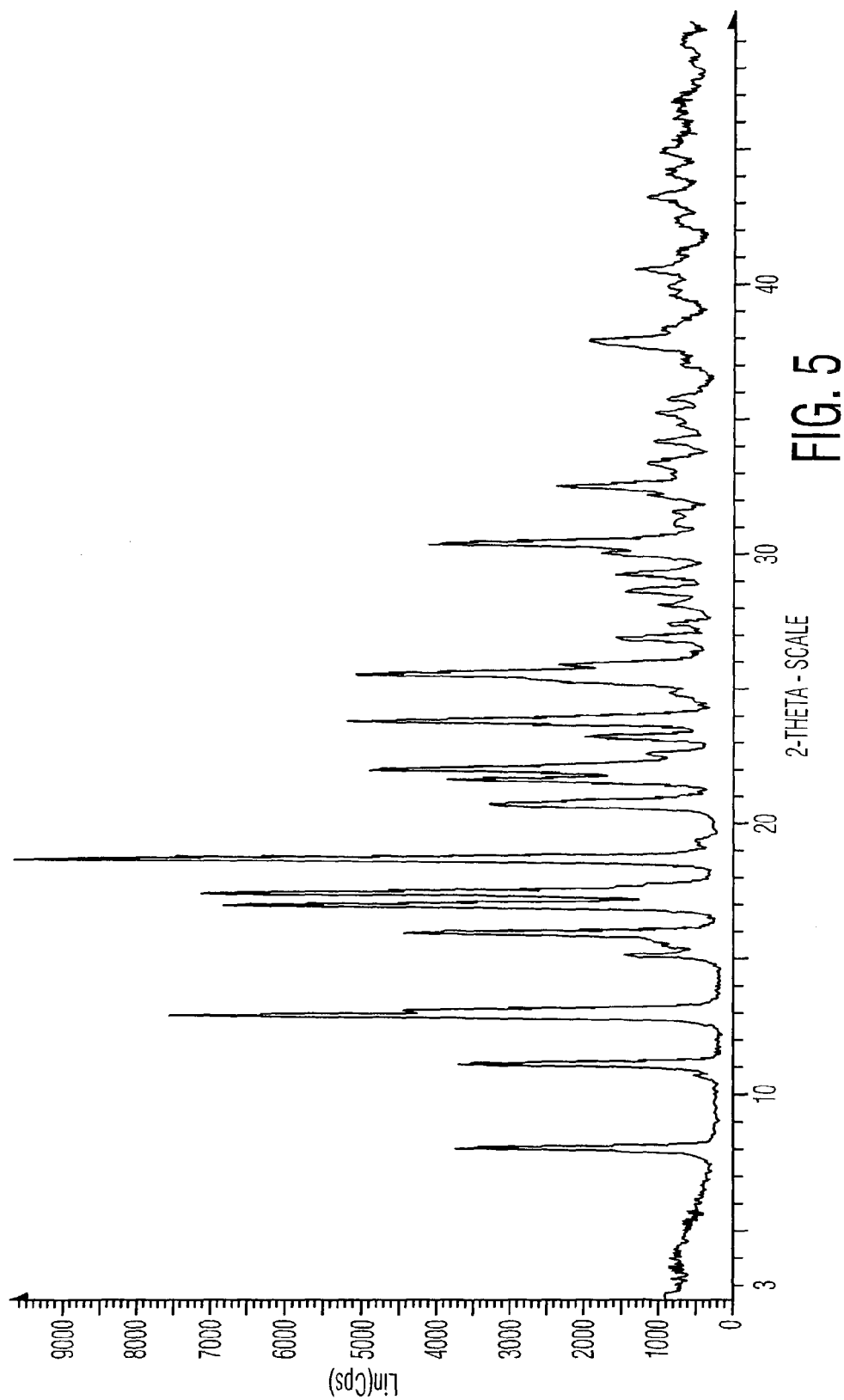
FIG. 5 is a graph of an x-ray powder diffraction pattern of crystalline polymorph Form 2 of Compound 13 crystallized from acetonitrile. The graph plots the intensity of the peaks as defined by counts per second versus the diffraction angle 2θ in degrees. The data were generated on a Bruker D8 diffractometer.
Figure 6:
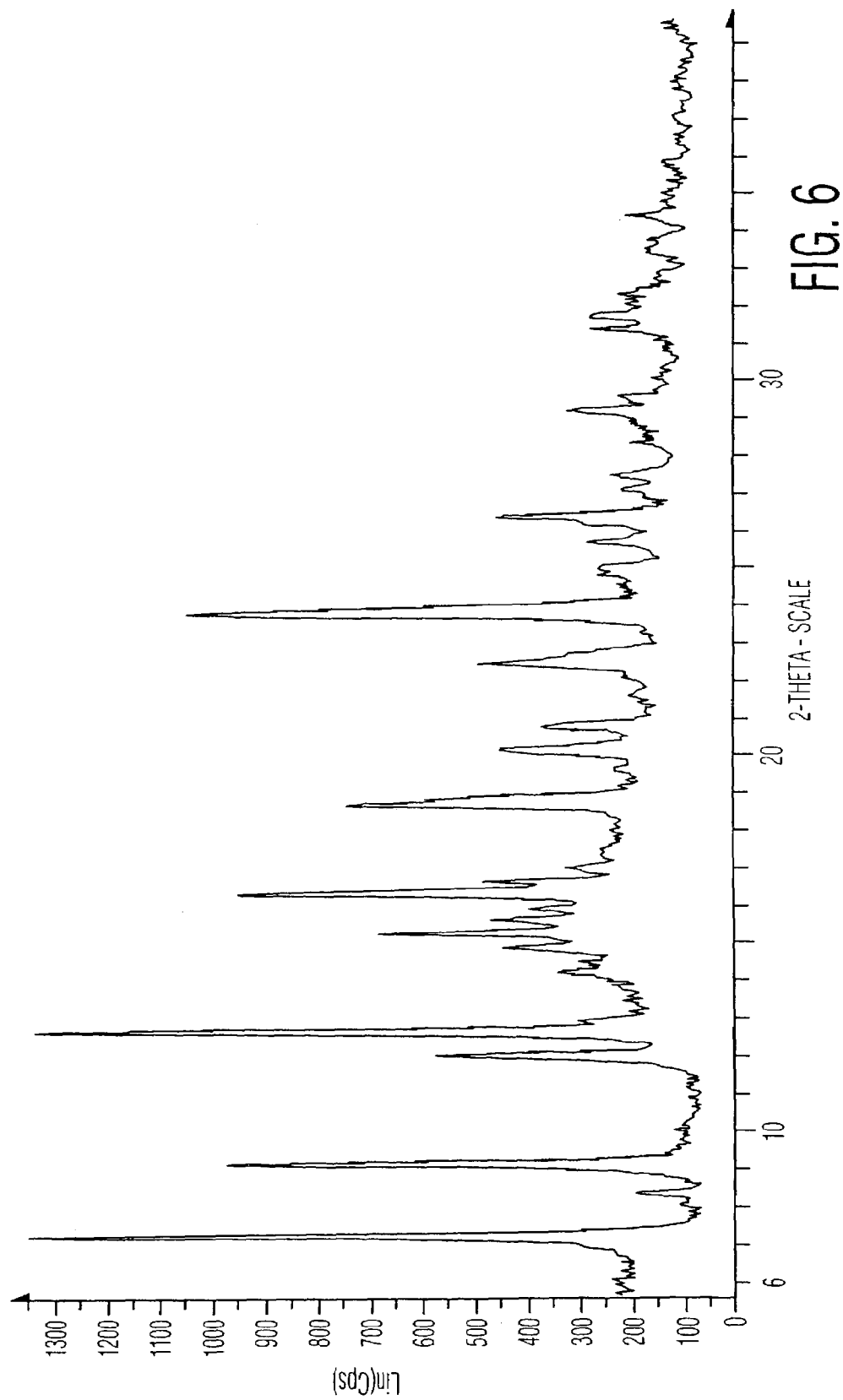
FIG. 6 is a graph of an x-ray powder diffraction pattern of crystalline polymorph Form 1 of Compound 13 crystallized from isopropanol/water. The graph plots the intensity of the peaks as defined by counts per second versus the diffraction angle 2θ in degrees. The data were generated on a Bruker D8 diffractometer.

Examples of XRPD data collected using the Bruker D8 are presented in FIGS. 5 and 6, which are XRPD patterns for Forms 2 and 1, respectively. Peak locations from patterns generated on the three instruments described above are given in Tables 3 and 4. Table 3 provides peak location data from five examples of XRPD patterns generated from Form 1 samples. The locations of nineteen characteristic peaks are presented for each example. The peak location data for each characteristic peak are further analyzed for average and standard deviations. Table 4 provides similar peak location data from six examples of XRPD patterns generated from Form 2 samples. The sample-to-sample variation is generally about +/−0.5 degrees 2θ, preferably about +/−0.3 degrees 2θ.

TABLE 3

FORM 1 POWDER X-RAY DIFFRACTION DATA PEAK LOCATIONS (DEGREES 2 θ)

| | EXAMPLE NUMBER: | | | | | RND. | | | | |
|---|---|---|---|---|---|---|---|---|---|---|---|
| | 1 | 2 | 3 | 4 | 5 | AVG. | AVG. | σ | 2 σ | RND 2 σ | MAX 2 σ |
| INST. | Rigaku Mini-Flex | Bruker D8 | Rigaku Mini-Flex | Rigaku Mini-Flex | Rigaku DMAX 2200 | | | | | | |
| PEAK NO. | | | | | | | | | | | |
| 1. | 7.341 | 7.224 | 7.481 | 7.401 | 7.26 | 7.341 | 7.3 | 0.10 | 0.21 | 0.2 | 0.3 |
| 2. | 8.419 | 8.293 | 8.523 | 8.518 | 8.34 | 8.419 | 8.4 | 0.10 | 0.21 | 0.2 | |
| 3. | 9.220 | 9.106 | 9.361 | 9.299 | 9.14 | 9.225 | 9.2 | 0.11 | 0.21 | 0.2 | |
| 4. | 12.719 | 12.633 | 12.841 | 12.820 | 12.64 | 12.731 | 12.7 | 0.10 | 0.20 | 0.2 | |
| 5. | 14.299 | 14.205 | 14.440 | 14.380 | 14.26 | 14.317 | 14.3 | 0.09 | 0.19 | 0.2 | |
| 6. | 14.960 | 14.872 | 15.100 | 15.020 | 14.90 | 14.970 | 15.0 | 0.09 | 0.18 | 0.2 | |
| 7. | 15.360 | 15.272 | 15.519 | 15.419 | 15.30 | 15.374 | 15.4 | 0.10 | 0.20 | 0.2 | |
| 8. | 16.439 | 16.632 | 16.580 | 16.520 | 16.38 | 16.456 | 16.5 | 0.09 | 0.19 | 0.2 | |
| 9. | 18.880 | 18.700 | 19.019 | 18.860 | 18.72 | 18.836 | 18.8 | 0.13 | 0.26 | 0.3 | |
| 10. | 20.200 | 20.150 | 20.340 | 20.340 | 20.14 | 20.234 | 20.2 | 0.10 | 0.20 | 0.2 | |
| 11. | 20.861 | 20.803 | 21.001 | 20.960 | 20.82 | 20.889 | 20.9 | 0.09 | 0.17 | 0.2 | |
| 12. | 23.980 | 23.900 | 24.140 | 23.980 | 23.92 | 23.984 | 24.0 | 0.09 | 0.19 | 0.2 | |
| 13. | 25.720 | 25.749 | 25.840 | 25.880 | 25.76 | 25.790 | 25.8 | 0.07 | 0.13 | 0.1 | |
| 14. | 26.261 | 26.443 | 26.400 | 26.520 | 26.44 | 26.413 | 26.4 | 0.10 | 0.19 | 0.2 | |

TABLE 3-continued

FORM 1 POWDER X-RAY DIFFRACTION DATA PEAK LOCATIONS (DEGREES 2 θ)

| | EXAMPLE NUMBER: | | | | | | RND. | | | | |
|---|---|---|---|---|---|---|---|---|---|---|---|
| | 1 | 2 | 3 | 4 | 5 | AVG. | AVG. | σ | 2 σ | RND 2 σ | MAX 2 σ |
| 15. | 27.200 | 27.184 | 27.320 | 27.341 | 27.18 | 27.245 | 27.2 | 0.08 | 0.16 | 0.2 | |
| 16. | 27.620 | 27.545 | 27.740 | 27.700 | 27.56 | 27.633 | 27.6 | 0.09 | 0.17 | 0.2 | |
| 17. | 29.060 | 29.320 | 29.200 | 29.419 | 29.28 | 29.256 | 29.3 | 0.13 | 0.27 | 0.3 | |
| 18. | 31.920 | 31.862 | 32.079 | 31.960 | 31.86 | 31.936 | 31.9 | 0.09 | 0.18 | 0.2 | |
| 19. | 34.579 | 34.508 | 34.640 | 34.640 | 34.54 | 34.581 | 34.6 | 0.06 | 0.12 | 0.1 | |

TABLE 4

FORM 2 POWDER X-RAY DIFFRACTION PEAK LOCATIONS (DEGREES 2 θ)

| | EXAMPLE NUMBER: | | | | | | | RND. | | | RND. 2 | |
|---|---|---|---|---|---|---|---|---|---|---|---|---|
| | 6 | 7 | 8 | 9 | 10 | 11 | AVG. | AVG. | σ | 2 σ | σ | MAX 2 σ |
| INST. | Rigaku Mini-Flex | Bruker D8 | Rigaku Mini-Flex | Rigaku Mini-Flex | Rigaku DMAX 2200 | Bruker D8 | | | | | | |
| PEAK NO. | | | | | | | | | | | | |
| 1. | 8.179 | 7.977 | 8.139 | 8.439 | 8.200 | 7.954 | 8.148 | 8.1 | 0.176 | 0.352 | 0.4 | 0.4 |
| 2. | 11.261 | 11.175 | 11.240 | 11.540 | 11.320 | 11.068 | 11.267 | 11.3 | 0.159 | 0.318 | 0.3 | |
| 3. | 13.081 | 12.851 | 13.059 | 13.359 | 13.120 | 12.886 | 13.059 | 13.1 | 0.183 | 0.366 | 0.4 | |
| 4. | 15.279 | 15.164 | 15.260 | 15.560 | 15.340 | 15.107 | 15.285 | 15.3 | 0.159 | 0.317 | 0.3 | |
| 5. | 16.141 | 15.993 | 16.100 | 16.420 | 16.180 | 15.492 | 16.129 | 16.1 | 0.168 | 0.337 | 0.3 | |
| 6. | 17.179 | 17.028 | 17.140 | 17.440 | 17.220 | 16.973 | 17.163 | 17.2 | 0.164 | 0.329 | 0.3 | |
| 7. | 17.659 | 17.430 | 17.600 | 17.919 | 17.680 | 17.442 | 17.622 | 17.6 | 0.180 | 0.361 | 0.4 | |
| 8. | 18.920 | 18.726 | 18.899 | 19.180 | 18.980 | 18.723 | 18.905 | 18.9 | 0.171 | 0.343 | 0.3 | |
| 9. | 20.900 | 20.948 | 20.880 | 21.200 | 20.940 | 20.735 | 20.934 | 20.9 | 0.151 | 0.303 | 0.3 | |
| 10. | 21.840 | 21.732 | 21.820 | 22.120 | 21.900 | 21.669 | 21.847 | 21.8 | 0.157 | 0.314 | 0.3 | |
| 11. | 22.221 | 22.039 | 22.219 | 22.500 | 22.280 | 22.050 | 22.218 | 22.2 | 0.169 | 0.339 | 0.3 | |
| 12. | 23.439 | 23.353 | 23.420 | 23.699 | 23.480 | 23.250 | 23.440 | 23.4 | 0.150 | 0.300 | 0.3 | |
| 13. | 24.200 | 24.095 | 24.000 | 24.461 | 24.100 | 23.854 | 24.118 | 24.1 | 0.204 | 0.409 | 0.4 | |
| 14. | 25.780 | 26.655 | 25.720 | 26.039 | 25.800 | 25.562 | 25.759 | 25.8 | 0.162 | 0.325 | 0.3 | |
| 15. | 30.640 | 30.547 | 30.600 | 30.880 | 30.680 | 30.450 | 30.633 | 30.6 | 0.145 | 0.290 | 0.3 | |

Referring to Table 3, peak numbers 1, 3 and 10, having average peak locations at 7.3, 9.2 and 20.2, respectively, are representative of Form 1. Referring to Table 4, peak numbers 1, 2, 6 and 11, having average peak locations at 8.1, 11.3, 17.2 and 22.2, respectively, are representative of Form 2. Peak numbers 7, 9 and 12 of Form 1, have average peak locations of 15.4, 18.8 and 24.0. These appear to roughly coincide with peak numbers 4, 8 and 13 of Form 2.

The DSC instrument used to test the polymorph samples was a Perkin-Elmere model Pryis 1 (manufactured in 1999), which came equipped with a refrigerated cooling system. The DSC cell/sample chamber was purged with 40 mL/min of ultra-high purity nitrogen gas. The instrument was calibrated with high purity indium. The accuracy of the measured sample temperature with this method is within about +/−1° C., and the heat of fusion can be measured within a relative error of about +/−5%. The samples were placed into a standard Perkin-Elmer aluminum DSC pan without a lid. Between about 3 mg and about 6 mg of polymorph sample powder was placed into the bottom of the pan and lightly tamped down to make contact with the pan. The weight of each sample was measured accurately and recorded to about a hundredth of a milligram. The instrument used an empty reference pan. The instrument was programmed to hold the sample at about 30° C. for about 1 minute before starting a 10° C./min dynamic heating ramp to about 300° C. The data were reported in units of "Watts/gram," which reflects the heat flow normalized by a sample weight. The normalized heat flow was plotted versus the measured sample temperature. The plots were made with the endothermic peaks pointing up. The endothermic melt peaks were evaluated for extrapolated onset and end (outset) temperatures, peak temperature, and heat of fusion in these analyses. The melt temperature and the heat required to melt a sample were unique for Form 2 of Compound 13 (FIG. 2) and Form 1 of Compound 13 (FIG. 4). Differential scanning calorimetry is discussed in the *Encyclopedia of Analytic Science*, Alan Townshend, ed., vol. 9, pp. 5155–5160, Academic Press, London (1995), which is incorporated herein by reference.

FIG. 2 shows a DSC pattern graph for Form 2 of Compound 13. This graph shows an endotherm beginning at 165.300° C. and ending at 171.729° C., which corresponds to the polymorph's melting point.

FIG. 4 shows a DSC pattern graph for Form 1 of Compound 13. This graph shows an endotherm beginning at 178.092° C. and ending at 181.022° C., which corresponds to the compound's melting point.

The preparation of Compound 13 is taught in WO 02/24698. An alternative process for preparing Compound 13 is taught in a copending U.S. patent application entitled Process for Preparing Xanthine Phosphodiesterase V Inhibitors and Precursors Thereof (Compound 13 is identified as Compound 13A in the copending application), which was filed on the same day as the present application and is incorporated herein in its entirety by reference. This process is depicted in Scheme I, which employs the following abbreviations: Me is methyl; Et is ethyl, OMe is methoxy, $M^+$ is a metal ion and OAc is acetate:
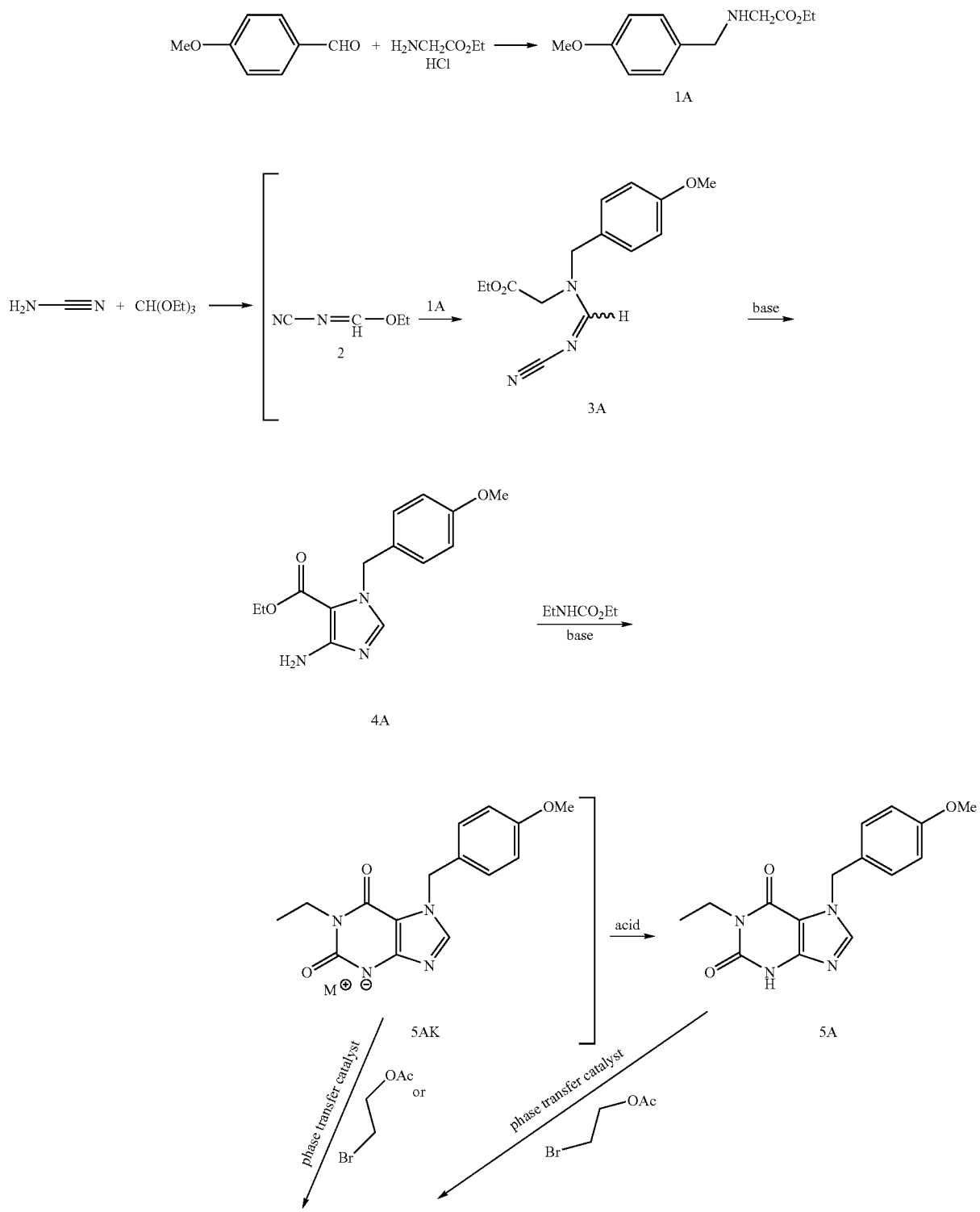
Scheme 1:
General Synthesis for Forms 1 and 2 Compound 13

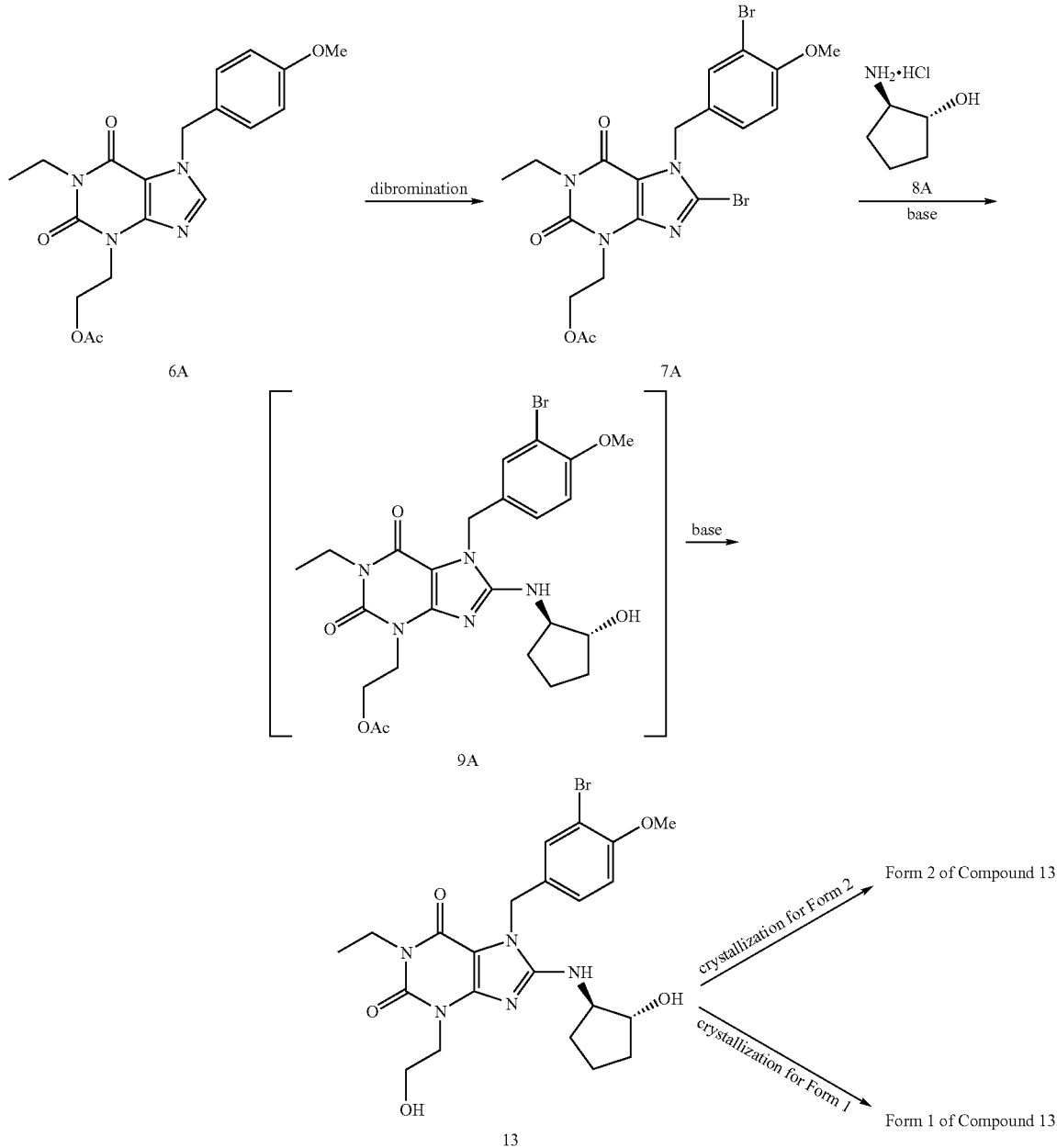

Using the process depicted in Scheme I will produce a crude Form 1 of Compound 13 before the final crystallization step. One can prepare pure Forms 1 or 2 of Compound 13 depending on the crystallization solvent in which the final step is carried out.

The crystallization of any form of Compound 13 to Form 2 of Compound 13 is preferably accomplished in an organic solvent selected from the group consisting of alcohols (e.g., methanol, ethanol, normal propyl alcohol, isopropyl alcohol, etc.), nitrites (e.g., acetonitrile, propionitrile, butionitrile, valeronitrile, benzonitrile, p-tolunitrile, etc.), esters (e.g., methyl acetate, ethyl acetate, normal propyl acetate, isopropyl acetate, etc.), ketones (e.g., methyl isobutyl ketone, acetone, etc.) and mixtures thereof. Higher homologs of the exemplified alcohols, nitriles, esters and ketones will also transform Compound 13 to Form 2 of Compound 13. More preferred solvents comprise isopropyl alcohol, acetonitrile, and mixtures thereof. The Form 2 crystallization step is carried out in an essentially non-aqueous solvent mixture, which for this step means a crystallizing solvent mixture comprising less than or equal to about 5%, preferably, less than or equal to about 2%, of water content by weight based on the weight of the crystallizing solvent mixture.

Crystallization can be carried out without the application of heat, but it is preferred that it is initiated upon the cooling of a heated saturated solution of Compound 13 dissolved in a crystallizing solvent. Generally, Compound 13 is put into a crystallizing solvent and heat is applied thereto until Compound 13 dissolves into solution. The heat applied can vary (e.g., heat sufficient to raise the solvent temperature to about 30–100° C.) depending on the process conditions and the concentration of Compound 13 in the crystallizing solvent. After the solution forms, the application of heat is continued to concentrate the solution (e.g., until about its super-saturation point). The concentrated solution is then cooled to provide the desired crystals.

It is also preferred to seed control the cooling of a saturated solution of Compound 13 in the Form 2 crystallizing solvent in order to minimize and/or prevent encrustation of product on the reactor walls (the sticking of crystallized particles to reactor walls), which can be difficult to remove. It is preferred that the Form 2 crystallization solution is seeded with a small amount (e g., about 0.2% w/w to about 1% w/w) of Form 2 of Compound 13 to help facilitate the conversion to Form 2, increase the yield of the batch, and avoid the potential of product encrustation on reactor walls. Encrustation of product on reactor walls will result in yield loss and solvent entrapment in the isolated crystallized product substance. The trapped solvent often cannot be lowered to a preferred level of about 0.1% w/w to about 0.2% w/w, even after prolonged drying. Seeding the batch at an appropriate time during crystallization will minimize and/or obviate this problem. Preferably, the batch is seeded at or around the super-saturation point; for acetonitrile crystallizing solvent, the super-saturation point would be around a concentration of about 7 volumes to about 8 volumes of solvent (1 g of solid per about 7 ml to about 8 ml of solvent).

The crystallization of Compound 13 to Form 1 of Compound 13 is preferably accomplished by dissolving Compound 13 in an organic solvent, then adding water. Preferred organic solvents comprise any of the Form 2 crystallizing solvents described above (i.e., alcohols, nitrites, esters and ketones). More preferred organic solvents comprise methanol and isopropanol. As for the Form 2 crystallizations described above, it is preferred to dissolve Compound 13 in a Form 1 crystallization organic solvent by heating the mixture until Compound 13 dissolves into solution, and continuing the heating until about the super-saturation point is reached. Then, water is added to precipitate the Form 1 crystals of Compound 13.

Alternatively, Form 1 of Compound 13 can be obtained by adding an anti-solvent (rather than water) to a solution of Compound 13 in a crystallization solvent. Preferred anti-solvents are hydrocarbons, such as hexane, heptane, toluene, xylene, and the like. For instance, hexane can be added to a solution of Compound 13 in an ester solvent (e.g., ethyl acetate, isopropyl acetate, and the like), and Form 1 of Compound 13 will precipitate out. The anti-solvent technique is generally preferable for isolating kinetic Form 1 of Compound 13. With regard to the organic solvent/followed by water technique, it is generally preferable to control crystallization conditions in order to isolate kinetic Form 1 of Compound 13. This can be accomplished by filtering the product as soon as possible (preferably, immediately) after crystallization has occurred.

Forms 1 and 2 of Compound 13 can be obtained from an amorphous form of Compound 13 or from another form of Compound 13 by choosing the appropriate crystallization procedure. For example, Form 2 of Compound 13 can be crystallized into Form 1 of Compound 13 by dissolving the former substance in an organic solvent, and adding water to that solution until Form 1 of Compound 13 precipitates out. Similarly, Form 2 of Compound 13 can be obtained from Form 1 of Compound 13 by crystallization in a Form 2 of Compound 13 crystallizing solvent.

As can be seen from a comparison of FIGS. 1 and 2 with FIGS. 3 and 4, respectively, Forms 1 and 2 exhibit different DSC and XRPD graphs. The two polymorphs also further differ in their water solubilities (Form 1: about 50 µg/mL vs. Form 2: about 30 µg/mL). Form 2 of Compound 13 is more thermodynamically stable than Form 1 of Compound 13 at process temperatures. Form 1 can equilibrate to Form 2 when slurried in one of the Form 2 crystallizing solvents (e.g., alcohol, nitrile, ester, etc.). For example, when a mixture of Form 1 of Compound 13 and Form 2 of Compound 13 is suspended in an organic crystallizing solvent (e.g., ethyl acetate, isopropanol, acetonitrile, and the like), and stored for an extended period of time (e.g., greater than or equal to about 10 hours), the Form 1 component of the mixture will convert to Form 2 of Compound 13.

Scheme II depicts preferred reaction conditions for the Scheme I steps utilized to prepare Forms 1 and 2 of Compound 13. Scheme II is also taught in a copending US patent application entitled Process for Preparing Xanthine Phosphodiesterase V Inhibitors and Precursors Thereof (Compound 13 is identified as Compound 13A in the copending application). Scheme II allows for an efficient, commercial scale preparation of Forms 1 and 2 of Compound 13, without the need for chromatographic purification of intermediates. The experimental conditions disclosed herein are preferred conditions, and one of ordinary skill in the art can modify them as necessary to achieve the same products. The following abbreviations are used in Scheme II: EtOH is ethanol; Me is methyl; Et is ethyl; Bu is butyl; n-Bu is normal-butyl, t-Bu is tert-butyl, OAc is acetate; KOt-Bu is potassium tert-butoxide; NBS is N-bromo suckinimine; NMP is 1-methyl-2-pyrrolidinone; DMA is N,N-dimethylacetamide; Bu$_4$NBr is tetrabutylammonium bromide; BU$_4$NOH is tetrabutylammonium hydroxide; and equiv is equivalents.

Scheme II:
Specific Syntheses of Forms 1 and 2 of Compound 13

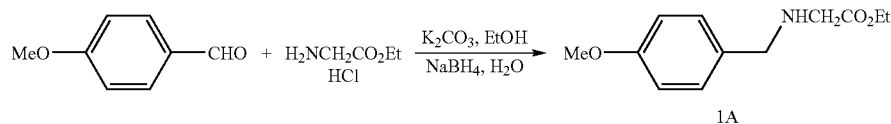

1A

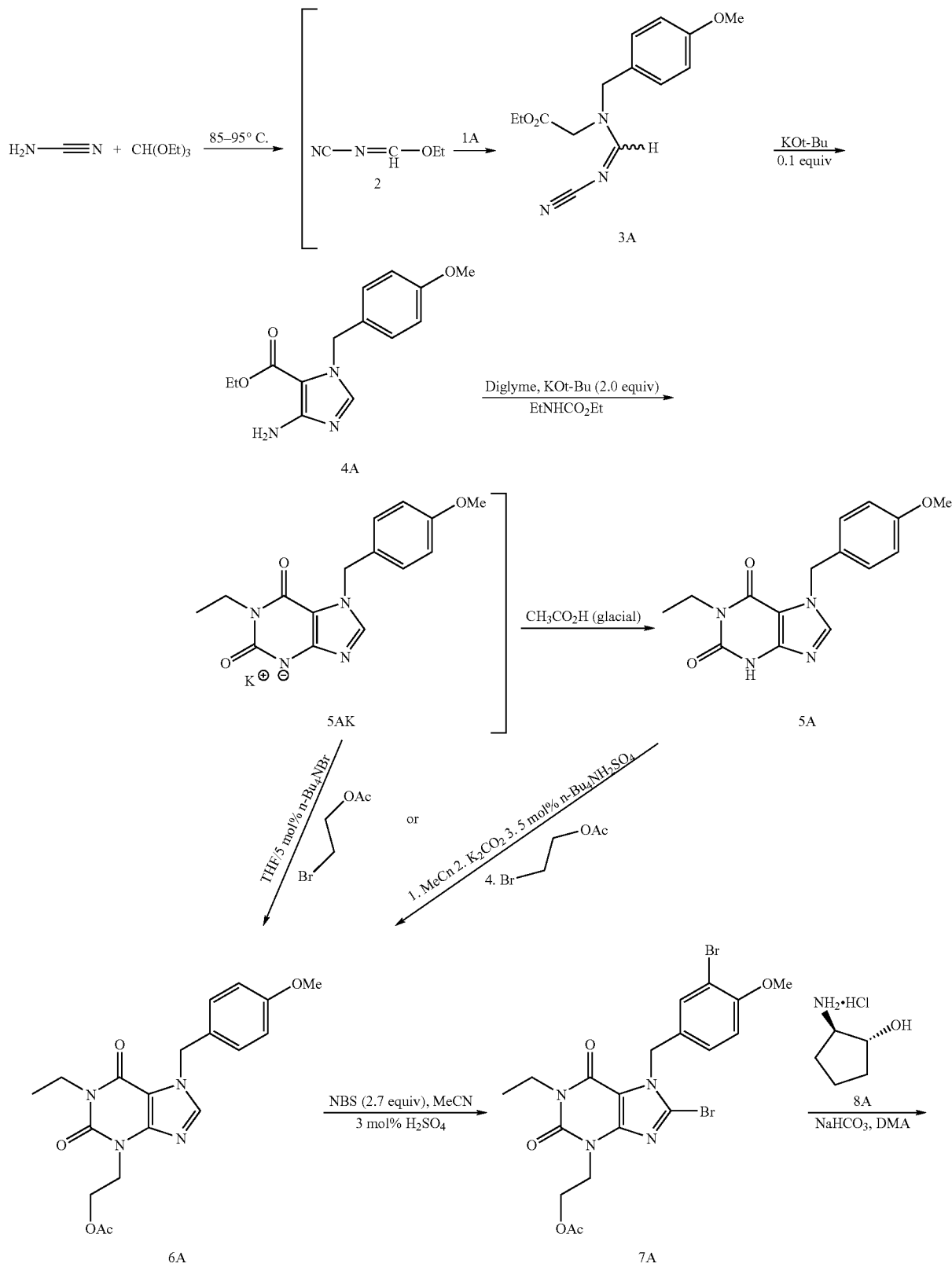

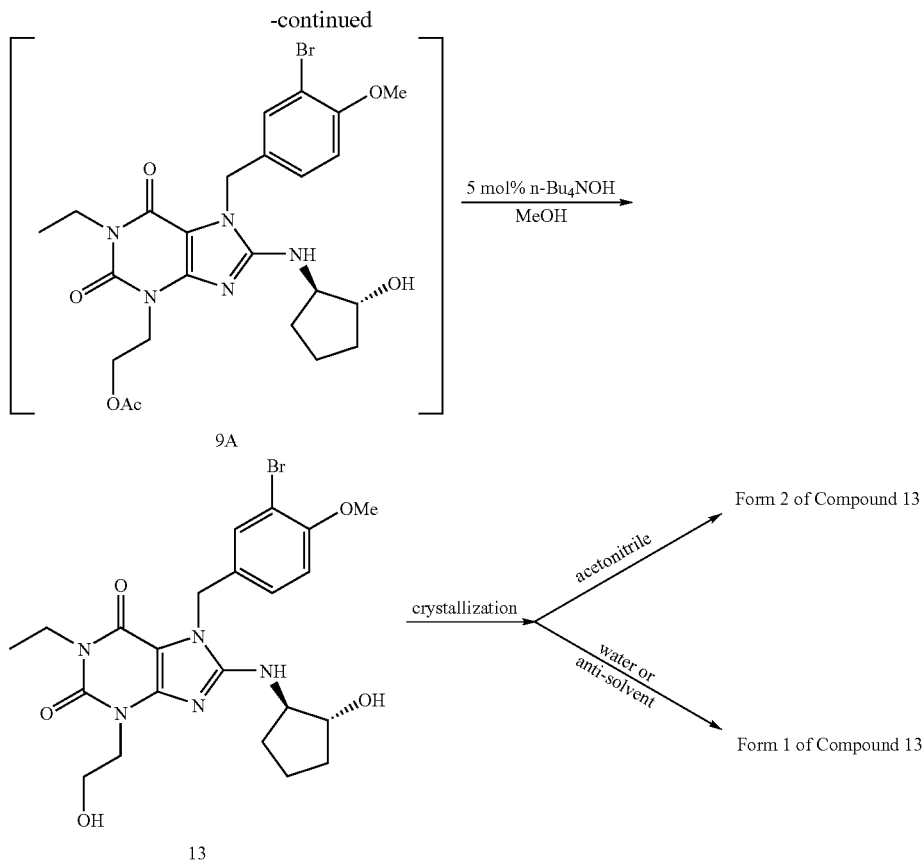

13

Compound Activity, Pharmaceutical Compositions and Methods of Use

Forms 1 and 2 of Compound 13 are each useful for inhibiting PDE V isoenzymes. Their isoenzyme activities (potencies) and isoenzyme selectivities can be measured by the PDE V $IC_{50}$ value, which is the concentration (in nM) of compound required to provide 50% inhibition of PDE V isoenzyme. The lower the value of PDE V $IC_{50}$, the more active is the compound to inhibiting the PDE V isoenzyme. Similarly, an $IC_{50}$ value may be obtained for other PDE isoenzymes, such as the PDE VI isoenzyme. Isoenzyme selectivity in this respect may be defined as the activity of a PDE inhibitor compound for a particular PDE isoenzyme as opposed to another PDE isoenzyme, for example, the activity of a compound to inhibit a PDE V isoenzyme compared to the activity of the same compound to inhibit a PDE VI isoenzyme. Once the PDE V $IC_{50}$ and PDE VI $IC_{50}$ values have been measured, one can calculate a selection ratio of PDE VI $IC_{50}$/PDE V $IC_{50}$, which is an indicator of isoenzyme selectivity—the larger the selection ratio, the more selective is the compound to inhibiting PDE V isoenzyme relative to PDE VI isoenzyme.

Forms 1 and 2 of Compound 13 each have a PDE V $IC_{50}$ of between about 2 nM and about 3 nM. These compounds are relatively highly potent inhibitors of the PDE V isoenzyme. In contrast, Forms 1 and 2 of Compound 13 each have a PDE VI $IC_{50}$ of greater than about 350 nM, which means they exhibit relatively low potency for inhibiting the PDE VI isoenzyme. The PDE V and VI $IC_{50}$ data allow for the calculation of an indicator for isoenzyme selectivity—the ratio of PDE VI $IC_{50}$/PDE V $IC_{50}$ (identified as "PDE VI/PDE V"). The higher the ratio of PDE VI/PDE V, the more selective is the compound for inhibiting PDE V isoenzyme relative to PDE VI isoenzyme. Forms 1 and 2 of Compound 13 each have a PDE VI/PDE V ratio of greater than about 140, which means they each exhibit relatively high selectivity for inhibiting the PDE V isoenzyme (relative to the PDE VI isoenzyme).

As can be seen from these data, Forms 1 and 2 of Compound 13 are potent (as measured by PDE V $IC_{50}$) and selective (as measured by PDE VI $IC_{50}$/PDE V $IC_{50}$) PDE V isoenzyme inhibitors. A skilled worker in the art would find the biological data significant, and along with the pharmaceutical properties of compositions comprising the inventive compounds, would find therapeutic uses for the inventive compounds in a number of applications, some of which are specified herein.

Forms 1 and 2 of Compound 13 each have at least one asymmetrical carbon atom. All isomers, including stereoisomers, enantiomers, tautomers and rotational isomers, are contemplated as being part of the invention. The invention comprises d- and l-isomers in pure form, and in admixture, including racemic mixtures. Isomers can be prepared using conventional techniques, either by reacting optically pure or optically enriched starting materials, or by separating isomers of the inventive compounds.

Forms 1 and 2 of Compound 13 can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

The invention comprises Forms 1 and/or 2 of Compound 13, a method for making either inventive compound, and methods for making and using a pharmaceutical composition comprising at least one inventive compound and at least one pharmaceutically-acceptable excipient or carrier to treat a variety of disorders, symptoms and diseases. The inventive compounds exhibited unexpectedly favorable properties with respect to PDE V isoenzyme activity and selectivity, which means they may be particularly useful for treating urogenital diseases, such as male and female sexual dysfunction, e.g., erectile dysfunction.

Forms 1 and 2 of Compound 13 can be formulated together with a pharmaceutically-acceptable excipient or carrier. The resulting compositions may be administered in vivo to mammals (e.g., men or women) and non-mammals to treat a variety of disease states (disorders, symptoms and diseases). For example, the inventive compounds and compositions may be used to treat diseases of the urogenital system, specifically, male erectile dysfunction (e.g., impotence) and female sexual dysfunction. Male erectile dysfunction may be defined as an inability of a male to sufficiently obtain, achieve and/or sustain a penile erection adequate to have intercourse with his mate. In the treatment of erectile dysfunction, it is believed that the inventive PDE V inhibitors are beneficial therapeutic agents because they elevate cGMP levels in the human body. Such an action may facilitate corpus cavernosum smooth muscle relaxation, which would provide an increased flow of blood therein, resulting in an erection. This makes the inventive compounds especially useful for treating impotence and other types of diseases that are affected by CGMP levels.

Accordingly, another aspect of the invention is a method for treating erectile dysfunction in a mammal in need of such treatment, comprising administering to the mammal at least one Form 1 of Compound 13 and/or at least one Form 2 of Compound 13, or a pharmaceutical composition thereof, in an amount effective to ameliorate and/or reduce one or more of the symptoms associated with erectile dysfunction sufficiently so that the patient can conduct and complete intercourse.

Introduced in 1998 as a treatment for impotence, Viagra® is currently the most commonly prescribed medication to treat physiologically-caused (male) erectile dysfunction ("MED" or "ED"). Certain patients, however, can experience undesirable side effects while taking Viagra®. For instance, it has been reported that Viagra® can cause a visual side effect by impairing the patient's color discrimination (blue/green), causing a "blue-halo" light visual alteration. This side effect is presumably due to inhibition of the PDE VI isoenzyme (found in a retina). See *Physicians' Desk Reference®*, 55th Ed, pp. 2534–37 (2001).

An advantage of Forms 1 and 2 of Compound 13 is that they can be particularly selective for the PDE V isoenzyme in comparison to other types of PDE isoenzymes, such as the PDE VI isoenzyme. It is believed that this increased selectivity will ameliorate side effects associated with the use of Viagra®. In particular, the high selectivity of the inventive compounds should minimize, and may even prevent, the occurrence of a "blue-halo" light visual alteration. It is believed that the increased isoenzyme selectivity in inhibiting PDE V isoenzyme (found in a penis) versus PDE VI isoenzyme (found in a retina) accounts for obviating the "blue-halo" visual side effect.

Forms 1 and 2 of Compound 13 can be employed alone or in combination with other active agents, particularly, other types of PDE inhibitors (especially cGMP PDE V inhibitors), prostanoids, α-adrenergic receptor, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, renin inhibitors, serotonin 5-$HT_{2c}$ receptor agonists, nociceptin receptor agonists, rho kinase inhibitors, potassium channel modulators and inhibitors of multidrug resistance protein 5. Examples of therapeutic agents that may be used in combination with Forms 1 and 2 of Compound 13 are the following: other types of PDE V inhibitors, such as sildenafil citrate (Viagra®, Pfizer, Connecticut, United States), Vardenafil™ (Bayer, Germany) and IC-351 (Cialis™, Lilly-ICOS, Washington and Indiana, United States); prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; and $ET_A$ antagonists, such as bosentan and ABT-627.

It is understood that combinations other than those described above may be undertaken with routine experimentation by one of ordinary skill in the art to treat mammalian disease states, while remaining within the scope of the invention. While Forms 1 and 2 of Compound 13 can each be used in an application of monotherapy to a patient, they also can be used in a combination therapy, in which one or both of them are administered in combination with one or more other pharmaceutical compounds (either separately or physically combined in a single form). The combination therapy is useful for treating a variety of disorders, symptoms and diseases, such as one or more of the mammalian disease states described above.

Due to their cGMP-PDE V inhibitory activities (as discussed above), Forms 1 and 2 of Compound 13 are useful for treating urological disorders, in particular, male and female sexual dysfunctions. Other physiological disorders, symptoms and diseases can also benefit from cGMP-PDE V inhibition. More specifically, the inventive compounds, and pharmaceutical compositions thereof, may be used to treat cardiovascular and cerebrovascular diseases, angina pectoris, hypertension, restenosis post angioplasty, endarterectomy, stent introduction, peripheral vascular diseases, cerebral stroke, respiratory tract disorders, such as reversible airway obstruction, chronic asthma and bronchitis, allergic disorders associated with atopy, such as urticaria, eczema, and rinitis, pulmonary hypertension, ischemic heart diseases, impaired glucose tolerance, diabetes and related complications, insulin resistance syndrome, hyperglycemia, polycystic ovarian syndrome, glomerular diseases, renal insufficiency, nephritis, tubular interstitial disease, autoimmune diseases, glaucoma, intestinal motility disorders, cachexia and cancer.

Another aspect of the invention is to provide a kit comprising separate containers in a single package, wherein inventive pharmaceutical compounds, and/or compositions are used ion combination with pharmaceutically-acceptable excipients or carriers to treat physiological disorders, symptoms and diseases in which cGMP-PDE V inhibition plays a role.

Pharmaceutically-Acceptable Dosage Forms

Forms 1 and 2 of Compound 13 can be administered to humans or other mammals by a variety of routes, including oral dosage forms and injections (intravenous, intramuscular, intraperitoneal, subcutaneous, and the like). Numerous other dosage forms comprising the inventive compounds can be readily formulated by one skilled in the art, utilizing the suitable pharmaceutical excipients or carriers as defined below. For considerations of patient compliance, oral dosage forms are generally most preferred.

The rate of systemic delivery can be satisfactorily controlled by one skilled in the art, by manipulating any one or more of the following:

(a) the active ingredient(s) proper;
(b) the pharmaceutically-acceptable excipient(s) or carrier(s), so long as the variants do not interfere in the activity of the particular active ingredient(s) selected;
(c) the type of excipient(s) or carrier(s), and the concomitant desirable thickness and permeability (swelling properties) of the excipient(s) or carrier(s);
(d) the time-dependent conditions of the excipient(s) or carrier(s);
(e) the particle size of the active ingredient; and
(f) the pH-dependent conditions of the excipient(s) or carrier(s).

Pharmaceutically-acceptable excipients or carriers comprise flavoring agents, pharmaceutical-grade dyes or pigments, solvents, co-solvents, buffer systems, surfactants, preservatives, sweetener agents, viscosity agents, fillers, lubricants, glidants, disintegrants, binders and resins.

Conventional flavoring agents can be used, such as those described in *Remington's Pharmaceutical Sciences*, $18^{th}$ Ed., Mack Publishing Co., 1288–1300 (1990), which is incorporated by reference herein. The pharmaceutical compositions of the invention generally comprise from 0% to about 2% of flavoring agent(s).

Conventional dyes and/or pigments can also be used, such as those described in the *Handbook of Pharmaceutical Excipients*, by the American Pharmaceutical Association & the Pharmaceutical Society of Great Britain, 81–90 (1986), which is incorporated by reference herein. The pharmaceutical compositions of the invention generally comprise from 0% to about 2% of dye(s) and/or pigment(s).

The pharmaceutical compositions of the invention generally comprise from about 0.1% to about 99.9% of solvent(s). A preferred solvent is water. Preferred co-solvents comprise ethanol, glycerin, propylene glycol, polyethylene glycol, and the like. The pharmaceutical compositions of the invention can comprise from 0% to about 50% of co-solvent(s).

Preferred buffer systems comprise acetic, boric, carbonic, phosphoric, succinic, malic, tartaric, citric, acetic, benzoic, lactic, glyceric, gluconic, glutaric and glutamic acids and their sodium, potassium and ammonium salts. Particularly preferred buffers are phosphoric, tartaric, citric and acetic acids and salts thereof. The pharmaceutical compositions of the invention generally comprise from 0% to about 5% of buffer(s).

Preferred surfactants comprise polyoxyethylene sorbitan fatty acid esters, polyoxyethylene monoalkyl ethers, sucrose monoesters and lanolin esters and ethers, alkyl sulfate salts and sodium, potassium and ammonium salts of fatty acids. The pharmaceutical compositions of the invention generally comprise from 0% to about 2% of surfactant(s).

Preferred preservatives comprise phenol, alkyl esters of parahydroxybenzoic acid, o-phenylphenol benzoic acid and salts thereof, boric acid and salts thereof, sorbic acid and salts thereof, chlorobutanol, benzyl alcohol, thimerosal, phenylmercuric acetate and nitrate, nitromersol, benzalkonium chloride, cetylpyridinium chloride, methyl paraben and propyl paraben. Particularly preferred preservatives are the salts of benzoic acid, cetylpyridinium chloride, methyl paraben and propyl paraben. The pharmaceutical compositions of the invention generally comprise from 0% to about 2% of preservative(s).

Preferred sweeteners comprise sucrose, glucose, saccharin, sorbitol, mannitol and aspartame. Particularly preferred sweeteners are sucrose and saccharin. Pharmaceutical compositions of the invention generally comprise from 0% to about 5% of sweetener(s).

Preferred viscosity agents comprise methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred viscosity agents are methylcellulose, carbomer, xanthan gum, guar gum, povidone, sodium carboxymethylcellulose, and magnesium aluminum silicate. Pharmaceutical compositions of the invention generally comprise from 0% to about 5% of viscosity agent(s).

Preferred fillers comprise lactose, mannitol, sorbitol, tribasic calcium phosphate, diabasic calcium phosphate, compressible sugar, starch, calcium sulfate, dextro and microcrystalline cellulose. Pharmaceutical compositions of the invention generally comprise from 0% to about 75% of filler(s).

Preferred lubricants/glidants comprise magnesium stearate, stearic acid and talc. Pharmaceutical compositions of the invention generally comprise from 0% to 7%, preferably, from about 1% to about 5%, of lubricant(s)/glidant(s).

Preferred disintegrants comprise starch, sodium starch glycolate, crospovidone and croscarmelose sodium and microcrystalline cellulose. Pharmaceutical compositions of the invention generally comprise from 0% to about 20%, preferably, from about 4% to about 15%, of disintegrant(s).

Preferred binders comprise acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. Pharmaceutical compositions of the invention generally comprise from 0% to about 12%, preferably, from about 1% to about 10%, of binder(s).

Additional agents known to a skilled formulator may be combined with the inventive compounds to create a single dosage form. Alternatively, additional agents may be separately administered to a mammal as part of a multiple dosage form.

A pharmaceutical composition typically comprises from about 0.1% to about 99.9% (by weight or volume, preferably, w/w) of active ingredient (Forms 1 and/or 2 of Compound 13), preferably, from about 5% to about 95%, more preferably, from about 20% to about 80%. For preparing pharmaceutical compositions comprising the inventive compound(s), inert, pharmaceutically acceptable excipients or carriers can be either solid or liquid. Solid form preparations comprise powders, tablets, dispersible granules, capsules, cachets and suppositories. Suitable solid excipients or carriers are known in the art, for example, magnesium carbonate, magnesium stearate, talc, sugar and lactose. Tablets, powders, cachets and capsules can be used as solid dosage forms suitable for oral administration. Examples of pharmaceutically-acceptable excipients or carriers and methods of manufacture for various compositions may be found in *Remington's Pharmaceutical Sciences*, $18^{th}$ Ed., Mack Publishing Co. (1990), which is incorporated in its entirety by reference herein.

Liquid form preparations comprise solutions, suspensions and emulsions. Common liquid form preparations comprise water and water-propylene glycol solutions for parenteral injection or addition of sweeteners and opacifiers for oral solutions, suspensions and emulsions. Liquid form preparations may also comprise solutions for intranasal administration.

Aerosol preparations suitable for inhalation comprise solutions and solids in powder form, which may be combined with a pharmaceutically acceptable excipient or carrier, such as an inert compressed gas (e.g., nitrogen).

Further included are solid form preparations that may be converted, shortly before use, to liquid form preparations for either oral or parenteral administration. Such liquid forms comprise solutions, suspensions and emulsions.

The compounds of the invention may also be delivered transdermally. The transdermal compositions can take the form of creams, lotions, aerosols and emulsions, and may be included in a transdermal patch of a matrix or reservoir type as is conventional in the art for this purpose.

The preferred mode of administering the compounds of the invention is oral. Preferably, the pharmaceutical preparation is in a unit dosage form. In such a form, the preparation is subdivided into suitable sized unit doses comprising appropriate quantities of the active component, for example, an effective amount to achieve the desired purpose.

The quantity of active ingredient (Forms 1 and/or 2 of Compound 13) in a unit dose of preparation may be varied or adjusted from about 0.01 mg to about 4,000 mg, preferably, from about 0.02 mg to about 2,000 mg, more preferably, from about 0.03 mg to about 1,000 mg, even more preferably, from about 0.04 mg to about 500 mg, and most preferably, from about 0.05 mg to about 250 mg, according to the particular application. A typical recommended daily dosage regimen for oral administration can range from about 0.02 mg to about 2,000 mg/day, in two to four divided doses. For convenience, the total daily dosage may be divided and administered in portions during the day as required. Typically, pharmaceutical compositions of the invention will be administered from about 1 time per day to about 5 times per day, or alternatively, as a continuous infusion. Such administration can be used as a chronic or acute therapy. The amount of active ingredient that may be combined with excipient or carrier materials to produce a single dosage form will vary depending upon the host treated and the particular mode of administration. As disclosed above, a typical preparation will comprise from about 0.1% to about 99.9% of active compound, preferably, from about 5% to about 95%, more preferably, from about 20% to about 80%. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The pharmaceutically-acceptable excipients or carriers employed in conjunction with the compounds of the present invention are used at a concentration sufficient to provide a practical size to dosage relationship. The pharmaceutically-acceptable excipients or carriers, in total, can comprise from about 0.1% to about 99.9% (by weight or volume, preferably, by w/w) of the pharmaceutical compositions of the invention, preferably, from about 5% to about 95% by weight, more preferably, from about 20% to about 80% by weight.

Upon improvement of a patient's condition, a maintenance dose of a compound, composition or combination of the invention can be administered, if desired or warranted. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art. The amount and frequency of the administration of Forms 1 and/or 2 of Compound 13, or the pharmaceutical compositions thereof, may be regulated according to the judgment of the attending clinician, based on the factors recited above. As a skilled artisan will appreciate, lower or higher doses than those recited above may be required.

For instance, it is often the case that a proper dosage level is based on the weight of the patient. For example, dosage levels of between about 0.01 mg/kg and about 100 mg/kg of body weight per day, preferably, between about 0.5 mg/kg and about 75 mg/kg of body weight per day, and more preferably, between about 1 mg/kg and about 50 mg/kg of body weight per day, of the inventive compound(s), and compositions described herein, are therapeutically useful for the treatment of a variety of biological disorders, particularly, male and female sexual dysfunction. Between two patients of differing weights, a higher dosage will be used for the heavier patient, all other things being equal.

Forms 1 and/or 2 of Compound 13 are understood to provide efficacious treatment of (male) erectile dysfunction, including a reasonable time of onset upon administration, and a reasonable duration after administration. For example, in the treatment of erectile dysfunction, a dosage of the inventive compound(s) can be taken about an hour before a sex act is to be undertaken. Particular dosages will work within about thirty minutes of their administration. Ideal dosages will affect a patient within about fifteen minutes of their administration. While food, diet, pre-existing conditions, alcohol and other systemic conditions could lengthen the time delay for an inventive drug to work after its administration, it is understood that optimum dosages in combination with sexual stimulation will result in an efficacious drug treatment within and for a reasonable amount of time.

Polymorph Purity

Preferably, the inventive polymorphs of Compound 13, Forms 1 and 2, are each substantially free of chemical impurities (e.g., by-products generated during the preparation of Forms 1 or 2 of Compound 13). "Substantially free" of chemical impurities for the purposes of this invention means less than or equal to about 5% w/w of chemical impurities, preferably, less than or equal to about 3% w/w of chemical impurities, more preferably, less than or equal to about 2% w/w of chemical impurities, and even more preferably, less than or equal to about 1% w/w of chemical impurities.

The inventive polymorphs of Compound 13 are, preferably, essentially free of other forms of Compound 13. "Essentially free" of other forms of Compound 13 for the purposes of this invention means less than or equal to about 15% w/w of other forms of Compound 13, preferably, less than or equal to about 10% w/w of other forms of Compound 13, more preferably, less than or equal to about 5% w/w of other forms of Compound 13, and even more preferably, less than or equal to about 2% w/w of other forms of Compound 13.

Preparation of Compound 13 in Form 1 and Form 2

Preparation 1: Form 1 of Compound 13

About 1 g of Compound 13 (in any form, both crystalline and non-crystalline) is dissolved into solution by heating it in about 5–10 volumes of an alcohol (e.g., methanol or isopropanol) to about the solution boiling point, and the solution is then filtered to remove any particulate matter. If desired, Darco can be added in the dissolution step to remove any color impurities from the batch. The solution is concentrated to about half the original volume, cooled to about room temperature, and diluted with about an equal volume of water. The precipitated solid is cooled, filtered, washed with about a 25% aqueous alcohol solution, and dried at about 70–80° C. under a vacuum to provide Form 1 of Compound 13.

Yield: about 90–95%.
Morphology: needles.
Melt Point: about 175–182° C.
Average DSC Heat of Fusion: about 70 J/g. See FIG. 4 which shows 71.112 J/g.
X-ray Powder Diffraction Angle [in degrees]: See Table 2 and FIG. 3.

Preparation 2A: Form 2 of Compound 13 Without Seeding

About 1 g of Compound 13 (in any form, both crystalline and non-crystalline) is dissolved by heating it in about 10–20 volumes of a Form 2 crystallizing solvent (e.g., alcohol, nitrile, ester or ketone). The solution is then filtered to remove any particulate matter. If desired, Darco can be added in the dissolution step to remove any color impurities from the batch. The solution is concentrated to about half of the original volume and cooled to about room temperature. The batch is then stirred at about room temperature for about 18 hours to obtain equilibrated pure Form 2 of Compound 13.

Yield: about 75–85%.
Morphology: plates.
Melt Point: about 164–172° C.
Average DSC Heat of Fusion: about 100 J/g. See FIG. 2 which shows 98.521 J/g.
X-ray Powder Diffraction Angle [in degrees]. See Table 1 and FIG. 1.

Preparation 2B: Form 2 of Compound 13 with Seeding

The batch is run in the same manner as described above for the preparation 2A up to the cooling of the solution to about room temperature. At this point, the solution is seeded with a small amount of Form 2 of Compound 13 solid (e.g., about 0.2% w/w to about 1% w/w based on the weight of starting material). The crystallized solid is then cooled, filtered, washed with crystallization solvent, and dried at about 70–80° C. under a vacuum to provide Form 2 of Compound 13. The yield obtained (about 90–95%) is a little more than is achieved in preparation 2A above (due to avoidance of product encrustation that occurs during preparation 2A).

The morphology, melt point, DSC heat of fusion and x-ray powder diffraction data are the same as shown below for Form 2 made by preparation 2A.

EXAMPLE

About 10 g of Form 1 of Compound 13 was added to and dissolved in about 17 volumes of acetonitirile by heating the batch to about 80–85° C. The batch was Darco treated to remove any color impurities. The hot solution was filtered to remove any particulate matter, and the batch was concentrated atmospherically to a final volume of about 6–7 volumes. About 0.05 g of Form 2 of Compound 13 seed (which is about 0.5% of the weight of initial charge of Form 1 of Compound 13) was added as a slurry in acetonitrile. The batch was gradually cooled to room temperature, held there for about 3 hours, and then cooled to about 0–5° C. The resulting suspension was filtered, washed with acetonitrile, and dried at about 70–80° C. in a vacuum to provide Form 2 of Compound 13 in about a 90–95% yield.

The morphology, melt point, DSC heat of fusion and x-ray powder diffraction data are the same as shown above for Form 2 made by preparation 2B.

Other than as shown in the operating example or as otherwise indicated, all numbers used in the specification and claims expressing quantities of ingredients, reaction conditions, and so forth, are understood as being modified in all instances by the term "about." The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A crystalline polymorph Form 2 of Compound 13:

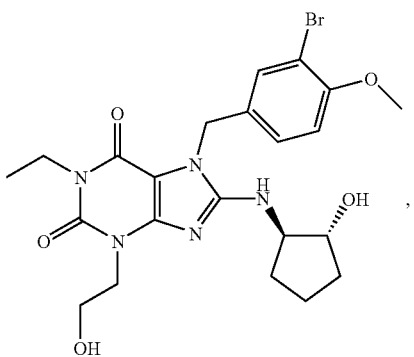

that exhibits an x-ray powder diffraction pattern having characteristic peak locations of 8.1, 11.3, 17.2, and 22.2 degrees 2θ+/−0.5 degrees 2θ.

2. A crystalline polymorph Form 2 of Compound 13:

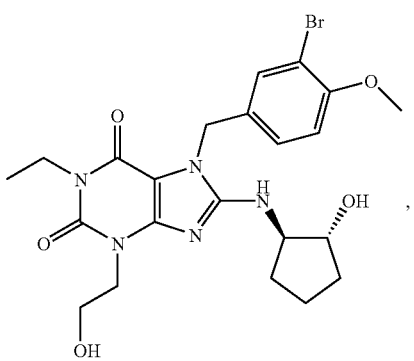

that exhibits an x-ray powder diffraction pattern having characteristic peak locations of 8.1, 11.3, 13.1, 15.3, 16.1, 17.2, 17.6, 18.9, 20.9, 21.8, 22.2, 23.4 24.1, 25.8 and 30.6 degrees 2θ+/−0.5 degrees 2θ.

3. A crystalline polymorph Form 2 of Compound 13:

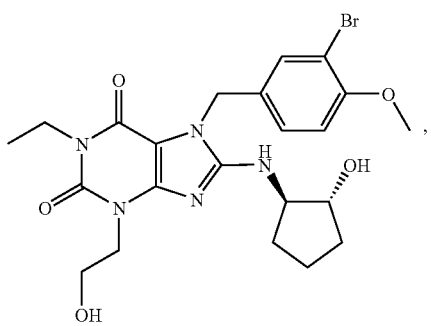

that exhibits an x-ray powder diffraction pattern substantially the same as the x-ray powder diffraction pattern shown in FIG. 5.

4. The crystalline polymorph of claim 1 further characterized in that it exhibits additionally a differential scanning calorimetry pattern substantially the same as the differential scanning calorimetry pattern shown in FIG. 2.

5. The crystalline polymorph of claim 1, which is prepared by crystallizing Compound 13 in an essentially non-aqueous solvent.

6. The crystalline polymorph of claim 5, wherein the essentially non-aqueous solvent is an organic solvent selected from the group consisting of alcohols, nitrites, esters, ketones, and mixtures thereof.

7. A pharmaceutical composition in solid dosage form comprising a crystalline polymorph Form 2 of Compound 13:

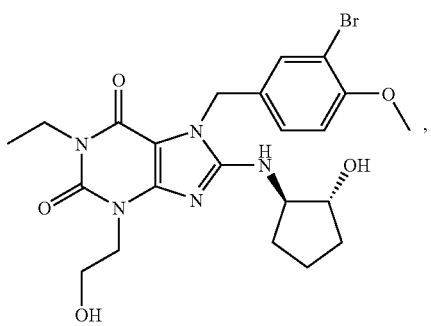

that exhibits an x-ray powder diffraction pattern having characteristic peak locations of 8.1, 11.3, 17.2, and 22.2 degrees 2θ+/−0.5 decrees 2θ, and at least one excipient or carrier.

8. The pharmaceutical composition of claim 7 further comprising at least one compound selected from the group consisting of: a prostanoid, α-adrenergic receptor, dopamine receptor agonist, melanocortin receptor agonist, endothelin receptor antagonist, endothelin converting enzyme inhibitor, angiotensin II receptor antagonist, angiotensin converting enzyme inhibitor, neutral metalloendopeptidase inhibitor, renin inhibitor, serotonin 5-HT$_{2c}$, receptor agonist, nociceptin receptor agonist, rho kinase inhibitor, potassium channel modulator and multidrug resistance protein 5 inhibitor.

9. A method for elevating a cGMP level in a patient in need of the elevation, comprising administering to the patient an effective amount of the crystalline polymorph according to claim 1.

10. A crystalline polymorph Form 1 of Compound 13:

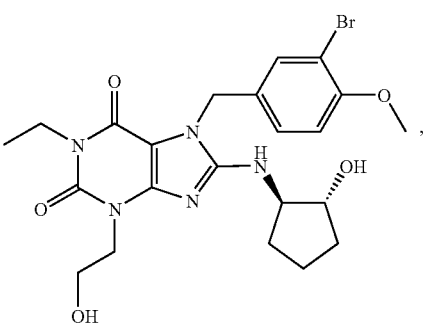

that exhibits an x-ray powder diffraction pattern having characteristic peak locations of 7.3, 9.2 and 20.2 degrees 2θ+/−0.5 degrees 2θ.

11. A crystalline polymorph Form 1 of Compound 13:

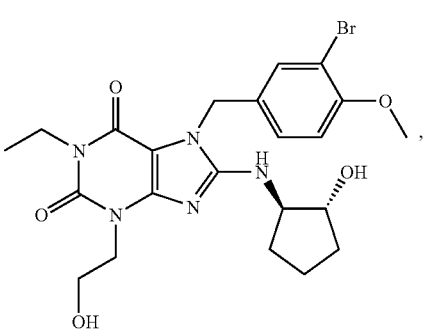

that exhibits an x-ray powder diffraction pattern having characteristic peak locations of 7.3, 8.4, 9.2, 12.7, 14.3, 15.0, 15.4, 16.5, 18.8, 20.2, 20.9, 24.0, 25.8, 26.4, 27.2, 27.6, 29.3, 31.9 and 34.6 degrees 2θ+/−0.5 degrees 2θ.

12. A crystalline polymorph Form 1 of Compound 13:

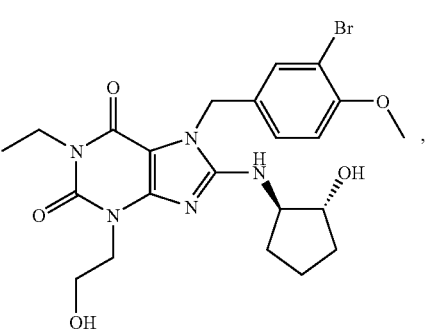

that exhibits an x-ray powder diffraction pattern substantially the same as the x-ray powder diffraction pattern shown in FIG. 6.

13. The crystalline polymorph of claim 10 further characterized in that it exhibits a differential scanning calorimetry pattern substantially the same as the differential scanning calorimetry pattern shown in FIG. 4.

14. The crystalline polymorph of claim 10, which is prepared by crystallizing Compound 13 by dissolving it in an organic solvent, and adding water thereto.

15. The crystalline polymorph of claim 14, wherein the organic solvent is selected from the group consisting of alcohols, nitriles, esters, ketones, and mixtures thereof.

16. The crystalline polymorph of claim 10, which is prepared by crystallizing Compound 13 by dissolving it in an ester, and adding an anti-solvent thereto.

17. The crystalline polymorph of claim 16, wherein the anti-solvent is a hydrocarbon selected from the group consisting of hexane, heptane, toluene and xylene.

18. A pharmaceutical composition in solid dosage comprising the a crystalline polymorph Form 1 of Compound 13:

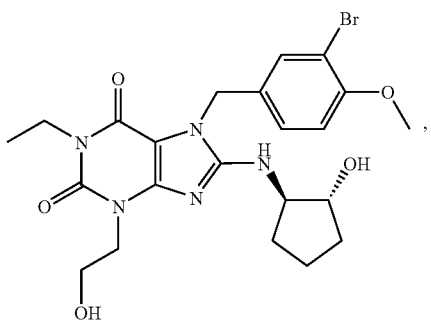

13 that exhibits an x-ray powder diffraction pattern having characteristic peak locations of 7.3, 9.2 and 20.2 degrees 2θ+/−0.5 degrees 2θ and at least one excipient or carrier.

19. The pharmaceutical composition of claim 18 further comprising at least one compound selected from the group consisting of: a prostanoid, α-adrenergic receptor, dopamine receptor agonist, melanocortin receptor agonist, endothelin receptor antagonist, endothelin converting enzyme inhibitor, angiotensin II receptor antagonist, angiotensin converting enzyme inhibitor, neutral metalloendopeptidase inhibitor, renin inhibitor, serotonin 5-$HT_{2c}$ receptor agonist, nociceptin receptor agonist, rho kinase inhibitor, potassium channel modulator and multidrug resistance protein 5 inhibitor.

20. A method for elevating a cGMP level in a patient in need of the elevation, comprising administering to the patient an effective amount of the crystalline polymorph according to claim 10.

21. A method for treating erectile dysfunction in a patient in need of the treatment, comprising administering to the patient an effective amount of the crystalline polymorph according to claim 1.

22. The method of claim 21 further comprising administering to the patient an effective amount of at least one compound selected from the group consisting of: a prostanoid, α-adrenergic receptor, dopamine receptor agonist, melanocortin receptor agonist, endothelin receptor antagonist, endothelin converting enzyme inhibitor, angiotensin II receptor antagonist, angiotensin converting enzyme inhibitor, neutral metalloendopeptidase inhibitor, renin inhibitor, serotonin 5-$HT_{2c}$ receptor agonist, nociceptin receptor agonist, rho kinase inhibitor, potassium channel modulator and multidrug resistance protein 5 inhibitor.

23. A method for treating pulmonary hypertension in a patient in need of the treatment, comprising administering to the patient an effective amount of the crystalline polymorph according to claim 1.

24. A method for treating erectile dysfunction in a patient in need of the treatment, comprising administering to the patient an effective amount of the crystalline polymorph according to claim 10.

25. The method of claim 24 further comprising administering to the patient an effective amount of at least one compound selected from the group consisting of: a prostanoid, α-adrenergic receptor, dopamine receptor agonist, melanocortin receptor agonist, endothelin receptor antagonist, endothelin converting enzyme inhibitor, angiotensin II receptor antagonist, angiotensin converting enzyme inhibitor, neutral metalloendopeptidase inhibitor, renin inhibitor, serotonin 5-$HT_{2c}$ receptor agonist, nociceptin receptor agonist, rho kinase inhibitor, potassium channel modulator and multidrug resistance protein 5 inhibitor.

26. A method for treating pulmonary hypertension in a patient in need of the treatment, comprising administering to the patient an effective amount of the crystalline polymorph according to claim 10.

* * * * *

UNITED STATES PATENT AND TRADEMARK OFFICE
CERTIFICATE OF CORRECTION

PATENT NO. : 7,192,962 B2  
APPLICATION NO. : 10/449650  
DATED : March 20, 2007  
INVENTOR(S) : Vilas H. Dahanukar et al.

Page 1 of 1

It is certified that error appears in the above-identified patent and that said Letters Patent is hereby corrected as shown below:

Col. 13, line 62, please correct "nitrites" to:

-- nitriles --

Claim 6, col. 29, line 32, please correct "nitrites" to:

-- nitriles --

Signed and Sealed this

Sixth Day of October, 2009

David J. Kappos  
*Director of the United States Patent and Trademark Office*